United States Patent [19]
Pagé et al.

[11] Patent Number: 6,030,818
[45] Date of Patent: Feb. 29, 2000

[54] BACTERIAL MASS PRODUCTION OF TAXANES AND PACLITAXEL

[75] Inventors: Michel Pagé, Québec; Nathalie Landry, St-Jean-Chrysostôme; Maurice Boissinot, St-Augustin; Marie-Claude Hélie, Cap-Rouge; Mario Harvey, St-Jean-Chrysostôme; Martin Gagné, Charlesbourg, all of Canada

[73] Assignee: BCM Développement, Inc., Quebec, Canada

[21] Appl. No.: 08/995,960

[22] Filed: Dec. 22, 1997

[51] Int. Cl.[7] ............................... C12N 1/20; C12P 17/02
[52] U.S. Cl. ................... 435/123; 435/252.1; 549/510; 549/511
[58] Field of Search ............................. 435/123, 252.1, 435/34; 549/510, 511

[56] References Cited

U.S. PATENT DOCUMENTS

| | | |
|---|---|---|
| 5,322,779 | 6/1994 | Strobel et al. . |
| 5,561,055 | 10/1996 | Pagé et al. . |
| 5,861,302 | 1/1999 | Stierle ................................. 435/254.1 |

FOREIGN PATENT DOCUMENTS

WO97/16200  5/1997  WIPO .

OTHER PUBLICATIONS

Wani MC et al., 1971, *J. Am. Chem. Soc.*, 93:2325–2327.
Nicolaou et al., 1994, *Nature*, 367:630–634.
Yukimune et al., 1996, *Nature Biotechnology*, 14:1129–1132.
Srinivasan et al., 1995, *Biotechnology and Bioengineering*, 47:666–676.
Strobel et al., 1996, *Microbiology*, 142:435–440.

*Primary Examiner*—Irene Marx
*Attorney, Agent, or Firm*—Nixon Peabody LLP

[57] ABSTRACT

The present invention relates to a method of obtaining different biologically pure cultures of bacteria isolated from different species of Taxus such as *Taxus canadensis, T. brevifolia, T. baccata, T. cuspidata,* and *T. hunnewelliana,* wherein the bacteria produce in vitro taxanes and paclitaxel, and wherein the bacteria are of the genus Sphingomonas, Bacillus, Pantoea or Curtobacterium. Also, the present invention relates to a method of a bacterial mass production of at least one taxane or paclitaxel. There is also disclosed a novel bacterial taxane. The present invention also relates to the use of different biologically pure cultures of bacteria isolated from different species of Taxus, wherein the bacteria are able to biotransform pro-taxanes. There is also provided a process for improving taxanes and paclitaxel production of taxanes and paclitaxel producing bacteria which include culturing bacteria in the presence of a mutagenic agent for a period a time sufficient to allow mutagenesis. There is disclosed two new mutated bacteria which have an increased yield of pro-taxane biotransformation.

15 Claims, 26 Drawing Sheets

Spectral Table

| # | Retention Time | Source | Spectrum Name | Baseline Correct | Searchable | Traceable |
|---|---|---|---|---|---|---|
| 1 | 35.820 | B.B. F2 def di | | On | Yes | Yes |
| 2 | 35.703 | 13-mix stds | 7-epi-10-deacetyltaxol | On | Yes | Yes |

Spectral Table

| # | Start Wvln | End Wvln | Resolution | Smooth | Derivative | Spline | Lambda Max | Maximum Absorbance |
|---|---|---|---|---|---|---|---|---|
| 1 | 200 | 350 | 2.4 | None | None | Off | 200.6 | 0.00501 |
| 2 | 200 | 350 | 2.4 | None | None | Off | 200.6 | 0.42673 |

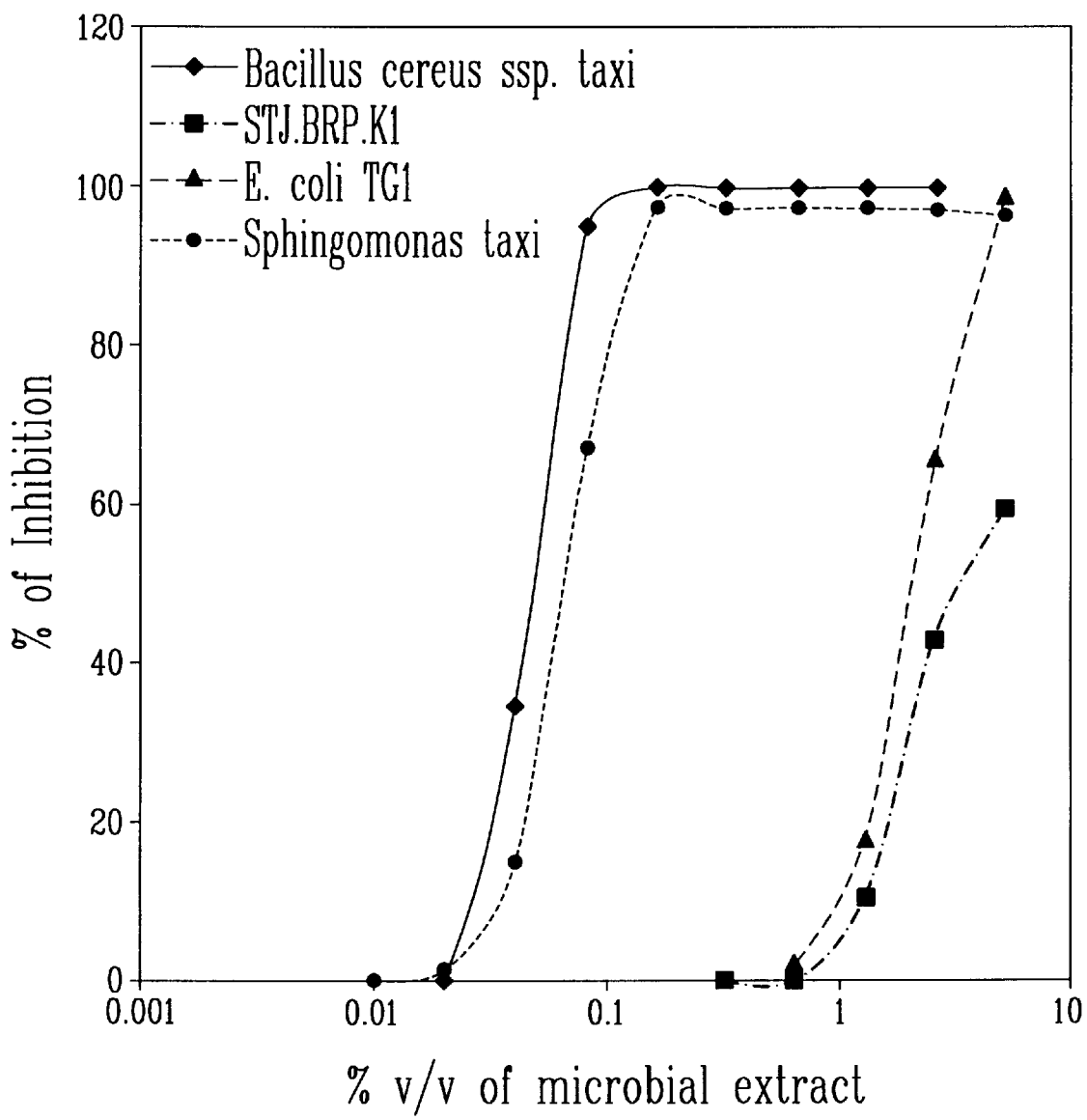

```
ATGATTACGC CAAGCTATTT AGGTGACACT ATAGAATACT CAAGCTATGC ATCCAACGCG    60
TTGGGAGCTC TCCCATATGG TCGACCTGCA GCGGCCCGCA CTAGTGATTA GAGTTTGATC   120
CTGGCTCAGA ACGAACGCTG GCGGCATGCC TAACACATGC AAGTCGAACG AGATCTTCGG   180
ATCTAGTGGC GCACGGGTGC GTAACGCGTG GGAATCTGCC CTTTGGTTCG GAATAACAGT   240
TGGAAACGAC TGCTAATACC GGATGATGAC GTAAGTCCAA AGATTTATCG CCAGAGGATG   300
AGCCCGCGTA GGATTAGCTA GTTGGTGTGG TAAGAGCGCA CCAAGGCGAC GATCCTTAGC   360
TGGTCTGAGA GGATGATCAG CCACACTGGA ACTGAGACAC GGCCCAGACT CCTACGGGAG   420
GCAGCAGTGG GGAATATTGG ACAATGGGCG AAAGCCTGAT CCAGCAATGC CGCGTGAGTT   480
GATGAAAGCC TTAGGTTGTT AAAGCTCTTT TACCCGGGAA TGATAATGAC AGTACCGGGA   540
GAATAAGCTC CGGCTAACTC CGTGCCAGCA GCCGCGGTAA TACGGAAGGA GCTAGCGTTG   600
TTCGGAATTA CTGGGCGTAA AGCGCACGTA GGCGGCTTTG TAAGTTAGAG GTGAAAGCCT   660
GGAGCTCAAC TCCAGAATTG CCTTTAAGAC TGCATCGCTT GAATCCAGGA GAGGTGAGTG   720
GAATTCCGAG TGTAGAGGTG AAATTCGTAG ATATTCGGAA GAACACCAGT GGCGAAGGCG   780
GCTCACTGGA CTGTATTGA. CGCTGAGGTG CGAAAGCGTG GGGAGCAAAC AGGATTAGAT   840
ACCCTGGTAG TCCACGCCGT AAACGATGAT AACTAGCTGT CCGGGACTT. GGTCTTTGGG   900
TGGCGCAGCT AACGCATTAA GTTATCCGCC TGGGGAGTAC GGCCGCAAGG TTAAAACTCA   960
AATGAATTGA CGGGGGCCTG CACAAGCGGT GGAGCATGTG GTTTAATTCG AAGCAACGCG  1020
CAGAACCTTA CCAGCGTTTG ACATGTCCGG ACGATTTCTG GAGACAGATC TCTTCCCTTC  1080
GGGGACTGGA ACGCAGGTGC ACATGGCTGT CGTCAGCTC. GTGTCGTGAG ATGTTGGGTT  1140
AAGTCCCGCA ACGAGCGCAA CCCTCGCCTT TAGTTACCAT CATTTAGTTG GGACTCTAA.  1200
AGGAACCGCC GGTGATAAGC CGGAGGAAGG TGGGGATGAC GTCAAGTCCT CATGCCCCTT  1260
ACGCGCTGGG CTACACACGT GCTACAATGG CGGTGACAGT GGGCAGCAAA CTCGCGAGAG  1320
TGCGCTAATC TCCAAAAGCC GTCTCAGTTC GGATTGTTCT CTGCAACTCG AGAGCATGAA  1380
GGCGGAATCG CTAGTAATCG GTCTAATCG. CGGATCAGCA TGCCGCGGTG AATACGTTCC  1440
ACACACCGCC CGTCACACCA TGGGAGTTGG GTTCACCCGA AGGCGTTGCG CTAACTCGTA  1500
AGAGAGGCAG GCGACCACGG GCGACCACGG GACTGGGGTG AAGTCGTAAC AAGGTA      1556
```

FIG. 8A

```
AGAGTTTGAT CATGGCTCAG GATGAACGCT GGCGGCGTGC CTAATACATG CAAGTCGAGC   60
GAATGGATTA AGAGCTTGCT CTTATGAAGT TAGCGGCGGA CGGGTGAGTA ACACGTGGGT  120
AACCTACCCA TAAGACTGGG ATAACTCCGG GAAACCGGGG CTAATACCGG ATAATATTTT  180
GAACTGCATA GTTCGAAATT GAAAGGCGGC TTCGGCTGTC ACTTATGGAT GGACCCGCGT  240
CGCATTAGCT AGTTGGTGAG GTAACGGCTC ACCAAGGCGA CGATGCGTAG CCGACCTGAG  300
AGGGTGATCG GCCACACTGG GACTGAGACA CGGCCCAGAC TCCTACGGGA GGCAGCAGTA  360
GGGAATCTTC CGCAATGGAC GAAAGTCTGA CGGAGCAACG CCGCGTGAGT GATGAAGGCT  420
TTCGGGTCGT AAAACTCTGT TGTTAGGGAA GAACAAGTGC TAGTTGAATA AGCTGGCACC  480
TTGACGGTAC CTAACCAGAA AGCCACGGCT AACTACGTGC CAGCAGCCCG CGGTAATACG  540
TAGGTGGCAA GCGTTATCCG GAATTATTGG GCGTAAAGCG CGCGCAGGTG GTTTCTTAAG  600
TCTGATGTGA AAGCCCACGG CTCAACCGTG GAGGGTCATT GGAAACTGGG AgACTTGAGT  660
GCAGAAGAGG AAAGTGGAAT TCCATGTGTA GCGGTGAAAT GCGTAgAGAT ATGGAGGAAC  720
ACCAGTGGCG AAGGCGACTT TCTGGTCTGT AACTGACACT GAGGCGCGAA AGCGTGGGGA  780
GCAAACAGGA TTAGATACCC TGGTAGTCCA CGCCGTAAAC GATGAGTGCT AAGTGTTAGA  840
GGGTTTCCGC CCTTTAGTGC TGAAGTTAAC GCATTAAGCA CTCCGCCTGG GGAGTACGGC  900
CGCAAGGCTG AAACTCAAAG GAATTGACGG GGGCCCGCAC AAGCGGTGGA GCATGTGGTT  960
TAATTCGAAG CAACGCGAAG AACCTTACCA GGTCTTGACA TCCTCTGAAA ACTCTAGAGA 1020
TAgAGCTTCT CCTTCGGGAG CAGAGTGACA GGTGGTGCAT GGTTGTCgTC AGCTCGTGTC 1080
GTGAGATGTT GGGTTAAGTC CCGCAACGAG CGCAACCCTT GATCTTAGTT GCCATCATTA 1140
AGTTGGGCAC TCTAAGGTGA CTGCCGGTGA CAAACCGGAG GAAGGTGGGG ATGACGTCAA 1200
ATCATCATGC CCCTTATGAC CTGGGCTACA CACGTGCTAC AATGGACGGT ACAAAGAGCT 1260
GCAAGACCGC GAGGTGGAGC TAATCTCATA AAACCGTTCT CAGTTCGGAT TGTAGGCTGC 1320
AACTCGCCTA CATGAAGCTG GAATCGCTAG TAATCGCGGA TCAGCATGCC GCGGTGAATA 1380
CGTTCCCGGG CCTTGTACAC ACCGCCCGTC ACACCACGAG AGTTTGTAAC ACCCGAAGTC 1440
GGTGGGGTAA CCTTTATGGA GCCAGCCGCC TAAGGTGGGA CAGATGATTG GGGTGAAGTC 1500
GTAACAAGGT AA                                                    1512
```

FIG. 8B

```
AGAGTTTGAT CCTGGCTCAG GATGAACGCT GGCGGCGTGC CTAATACATG CAAGTCGAGC    60
GAACTGATTA GAAGCTTGCT TCTATGACGT TAGCGGCGGA CGGGTGAGTA ACACGTGGGC   120
AACCTGCCTG TAAGACTGGG ATAACTTCGG GAAACCGAAG CTAATACCGG ATAGGATCTT   180
CTCCTTCATG GGGGATGATT GAAAGATGGT TTCGGCTATC ACTTACAGAT GGGCCCGCGG   240
TGCATTAGCT AGTTGGTGAG GTAACGGCTC ACCAAGGCTC CGATGCATAG CCGACCTGAG   300
AGGGTGATCG GCCACACTGG GACTGAGACA CGGCCCAAAC TCCTACGGGA GGCAGCAGTA   360
GGGAATCTTC CGCAATGGAC GAAAGTCTGA CGGAGCAACG CCGCGTGAGT GATGAAGGCT   420
TTCGGGTCCT AAAACTCTGT TGTTnGGGAA GAACAAATAC CAGAGTAACT GCTTGTTCCT   480
TGACGGTACC TAACCAGAAA GCCACGGCTA ACTACTTTCC AGCAGCCCGC GTAATACnTA   540
TGTTGGCAAG CGTTATCCGG AATTATTGGG CGTTAAAGC GCGCGCAGG CGTTTCTTA    600
AGTCTGATGT GAAAGCCCAC GGCTCAACCG TGGAGGGTCA TTGGAAACTG GGGAACTTGA   660
GTGCAGAAGA GAAAAGCGGA ATTCCACGTG TAGCGGTGAA ATGCGTAGAG ATGTGGAGGA   720
ACACCAGTGG CGAAGGCGGC TTTTTGGTCT GTAACTGACG CTGAGGCGCG AAAGCGTGGG   780
GAGCAAACAG GATTAGATAC CCTGGTAGTC CACGCCGTAA ACGATGAGTG CTAAGTGTTA   840
GAGGGTTTCC GCCCTTTAGT GCTGCAGCTA ACGCATTAAG CACTCCGCCT GGGGAGTACG   900
GTCGCAAGAC TGAAACTCAA AGGAATTGAC GGGGCCCGC ACAAGCGGTG GAGCATGTGG    960
TTTAATTCGA AGCAACGCGA AGAACCTTAC CAGGTCTTGA CATCCTCTGA CAACTCTAGA  1020
GATAGAGCGT TCCCCTTCGG GGGACAGAGT GACAGGTGGT GCATGGTTGT CGTCAGCTCG  1080
TGTCgTGAGA TgTTGGGTtA AGTCCCGCAA CGAGCGCAAC CCTTGATCTT AGTTGCCAgC  1140
ATTTAGTTGG GCACTCTAAG GTGACTGCCG GTGACAAACC GGAGGAAGGT GGGGATGACG  1200
TCAAATCATC ATGCCCCTTA TGACCTGGGC TACACACGTG CTACAATGGA TGGTACAAAG  1260
GGCTGCAAGA CCGCGAGGTC AAGCCAATCC CATAAAACCA TTCTCAGTTC GGATTGTAGG  1320
CTGCAACTCG CCTACATGAA GCTGGAATCG CTAGTAATCG CGGATCAGCA TGCCGCGGTG  1380
AATACGTTCC CGGGCCTTGT ACACACCGCC CGTCACACCA CGAGAGTTTG TAACACCCGA  1440
AGTCGGTGGA GTAACCGTAA GGAGCTAGCC GCCTAAGGTG GGACAGATGA TTGGGGTGAA  1500
GTCGTAACAA GGTAA                                                  1515
```

FIG. 8C

| | | | | |
|---|---|---|---|---|
| TCGGGACGGT | CAGCACACGA | GGAGCTTGCT | CCTTGGGTGA | CGAGTGGCGG | ACGGGTGAGT | 60 |
| AATGTCTGGG | GATCTGCCCG | ATAnAGGGGG | ATAACCACTG | GAAACGGTGG | CTAATACCGC | 120 |
| ATAACGTCGC | AAGACCAAAG | AGGGGGACCT | TCGGGCCTCT | CACTATCGGA | TGAACCCAGA | 180 |
| TGGGATTAGC | TAGTAnGCGG | GGTAATGGCC | CACCTAGGCG | ACGATCCCTA | nCTGGTCTGA | 240 |
| GAGGATGACC | AGCCACACTG | GAACTGAGAC | ACGGTCCAnA | CTCCTACGGG | AGGCAGCAGT | 300 |
| GGGGAATATT | GCACAATGGG | CGCAAGCCTG | ATGCAGCCAT | GCCGCGTGTA | TGAAGAAGGC | 360 |
| CTTCGGGTTG | TAAAGTACTT | TCAGCGGGGA | GGAAGGCGAT | GCGGTTAATA | ACCCTGTCGA | 420 |
| TTGACGTTCC | CCGCAnGAAG | AAGCACCGGC | TAACTCCGTG | CCAGCAGCCG | CGGTAATACC | 480 |
| GGAGGGTGCA | AGCGTTAATC | CGGAATTACT | GGGCGTAAAG | CGCACGCAGG | CGGTCTGTTA | 540 |
| AGTCAGATGT | GAAATCCCCG | GGCTTAACCT | GGGAACTGCA | TTTGAAACTG | GCAGGCTTGA | 600 |
| GTCTTGTAGA | GGGGGGTAGA | ATTCCAGGTG | TAGCGGTGAA | ATGCGTAGAG | ATCTGGAGGA | 660 |
| ATACCGGTGG | CGAAGGCGGC | CCCCTGGACA | AAGACTGACG | CTCAGGTGCG | AAAGCGTGGG | 720 |
| GAGCAAACAG | GATTAGATAC | CCTGGTAGTC | CACGCCGTAA | ACGATGTCGA | CTTGGAGGTT | 780 |
| GTTCCCTTGA | GGAGTGGCTT | CCGGAGCTAA | CGCGTTAAGT | CGACCGCCTG | GGGAGTACGG | 840 |
| CCGCAAGGTT | AAAATTCAAA | TGAATTGACG | GGGGCCCGCA | CAAGCGGTGG | AGCATGTGGT | 900 |
| TTAATTCGAT | GCAACGCGAA | GAACCTTACC | TACTCTTGAC | ATCCAGCGAA | CTTGCCAGAG | 960 |
| ATGGATTGGT | GCCTTCGGGA | ACGCTGAGAC | AGGTGCTGCA | TGGCTGTCGT | CAGCTCGTGT | 1020 |
| TGTGAAATGT | TGGGTTAAGT | CCCGCAACGA | GCGCAACCCT | TATCCTTTGT | TGCCAGCGAT | 1080 |
| TCGGTCGGGA | ACTCAAAGGA | GACTGCCGGT | GATAAACCGG | AGGAAGGTGG | GGATGACGTC | 1140 |
| AAGTCATCAT | GGCCCTTACG | AGTAGGGCTA | GCGCAACCGC | ACAAGTGCT | ACAAAGAGAG | 1200 |
| AAGCGACCTC | GCGAGAGCAA | GCGGACCTCA | CAAAGTGCGT | CGTAGTCCGG | ATCGGAGTCT | 1260 |
| GCAACTCGAC | TCCGTGAAGT | CGGAATCGCT | AGTAATCGTG | GATCAGAATG | CCACGGTGAA | 1320 |
| TACGTTCCCG | GGCCTTGTAC | ACACCGCCCG | TCACACCATG | GGAGTGGGTT | GCAAAGAAGT | 1380 |
| TAGGTAGCTT | AACCTTCGGG | AGGGCGCTTA | CCACTTTGTG | ATTCATGACT | GGGGTGAAGT | 1440 |
| CGTAACAAGT | A | | | | | 1451 |

FIG. 8D

```
AGAGTTTGAT CCTGGCTCAG GATGAACGCT GGCGGCGTGC CTAATACATG CAAGTCGAGC    60
GAATGGATTG AGAGCTTGCT CTCAAGAAGT TAGCGGCGGA CGGGTGAGTA ACACGTGGGT   120
AACCTGCCCA TAAGACTGGG ATAACTCCGG GAAACCGGGG CTAATACCGG ATAACATTTT   180
GAACTGCATG GTTCGAAATT GAAAGGCGGC TTCGGCTGTC ACTTATGGAT GGACCCGCGT   240
CGCATTAGCT AGTTGGTGAG GTAACGGCTC ACCAAGGCAA CGATGCGTAG CCGACCTGAG   300
AGGGTGATCG GCCACACTGG GACTGAGACA CGGCCCAGAC TCCTACGGGA GGCAGCAGTA   360
GGGAATCTTC CGCAATGGAC GAAAGTCTGA CGGAGCAACG CCGCGTGAGT GATGAAGGCT   420
TTCGGGTCGT AAAACTCTGT TGTTAGGGAA GAACAAGTGC TAGTTGAATA AGCTGGCACC   480
TTGACGGTAC CTAACCAGAA AGCCACGGCT AACTACGTGC CAGCAGCCGC GGTAATACGT   540
AGTGTGCAAG CGTTATCCGG AATTATTGGG CGTAAAGCGC GCGCAGGTGG TTTCTTAGGT   600
CTGATGTGAA AGCCCACGGC TCAACCGTGG AGGGTCATTG GAAACTGGGA GACTTGAGTG   660
CAGAAGAGGA AAGTGGAATT CCATGTGTAG CGGTGAAATG CGTAGAGATA TGGAGGAACA   720
CCAGTGGCGA AGGCGACTTT CTGGTCTGTA ACTGACACTG AGGCGCGAAA GCGTGGGGAG   780
CAAACAGGAT TAGATACCCT GGTAGTCCAC GCCGTAAACG ATGAGTGCTA AGTGTTAGAG   840
GGTTTCCGCC CTTTAGTGCT GAAGTTAACG CATTAAGCAC TCCGCCTGGG GAGTACGGCC   900
GCAAGGCTGA AACTCAAAGG AATTGACGGG GGCCCGCACA AGCGGTGGAG CATGTGGTTT   960
AATTCGAAGC AACGCGAAGA ACCTTACCAG GTCTTGACAT CCTCTGAAAA CCCTAGAGAT  1020
AGGGCTTCTC CTTCGGGAGC AGAGTGACAG GTGGTGCATG GTTGTCGTCA GCTCGTGTCG  1080
TGAGATGTTG GGTTAAGTCC CGCAACGAGC GCAACCCTTG ATCTTAGTTG CCATCATTAA  1140
GTTGGGCACT CTAAGGTGAC TGCCGGTGAC AAACCGGAGG AAGGTGGGGA TGACGTCAAA  1200
TCATCATGYC CCTTATGACC TGGGCTACAC ACGTGCTACA ATGGACGGTA CAAAGAGCTG  1260
CAAGACCGCG AGGTGGAGCT AATCTCATAA AACCGTTCTC AGTTCrGATT GTAGGCTGCA  1320
ACTCGCCTAC ATGAAGCTGG AATCGCTAGT AATCGCGGAT CAGCATGCCG CGGTGAATAC  1380
GTTCCCGGGC CTTGTACACA CCGCCCGTCA CACCACGAGA GTTTGTAACA CCCGAAGTCG  1440
GTGGGGTAAC CTTTTTGGAG CCAGCCGCCT AAGGTGGGAC AGATGATTGG GGTGAAGTCG  1500
TAACAAGGTA GCC                                                     1513
```

FIG - 8E

```
AGAGTTTGAT CCTGGCTCAG GACGAACGCT GGCGGCGTGC CTAATACATG CAAGTCGAGC    60
GAACAGATGG GAGCTTGCTC CCTGATGTTA GCGGCGGACG GGTGAGTAAC ACGTGGGTAA   120
CCTGCCTGTA AGACTGGGAT AACTCCGGGA AATCGGGGCT AATACCGGAT GGTTGTTTGA   180
ACCGCATGGT TCAGACATAA AAGGTGGCTT CGGCTACCAC TTACAGATGG ACCCGCGGCG   240
CATTAGCTAG TTGGTGAGGT AACGGCTCAC CAAGGCGACG ATGCGTAGCC GACCTGAGAG   300
GGTGATCGGC CACACTGGGA CTGAGACACG GCCCAGACTC CTACGGGAGG CAGCAGTAGG   360
GAATCTTCCG CAATGGACGA AAGTCTGACG GAGCAACGCC GCGTGAGTGA TGAAGGTTTT   420
CGGATCGTAA AGCTCTGTTG TTAGGGAAGA ACAAGTGCCG TTCAAATAGG GCGGCACCTT   480
GACGGTACCT AACCAGAAAG CCACGGCTAA CTACGTGCCA GCAGCCGCGG TAATACGTAG   540
GTGGCAAGCG TTGTCCGGAA TTATTGGGCG TAAAGGGCTC GCAGGCGGTT TCTTAAGTCT   600
GATGTGAAAG CCCCCGGTTC AACGGGGGAG GGTCATTGGA AACTGGGGAA CTTGAGTGCA   660
GAAGAGGAGA GTGGAATTCC ACGTGTAGCG GTGAAATGCG TAGAGATGTG GAGGAACACC   720
AGTGGCGAAG GCGACTCTCT GGTCTGTAAC TGACGCTGAG GAGCGAAAGC GTGGGGAGCG   780
AACAGGATTA GATACCCTGG TAGTCCACGC CGTAAACGAT GAGTGCTAAG TGTTAGGGGG   840
TTTCCGCCCC TTAGTGCTGC AGCTAACGCA TTAAGCACTC CGCCTGGGGA GTACGGTCGC   900
AAGACTGAAA CTCAAAGGAA TTGACGGGGG CCCGCACAAG CGGTGGAGCA TGTGGTTTAA   960
TTCGAAGCAA CGCGAAGAAC CTTACCAGGT CTTGACATCC TCTGACAATC CTAGAGATAG  1020
GACGTCCCCT TCGGGGGCAG AGTGACAGGT GGTGCATGGT TGTCGTCAGC TCGTGTCGTG  1080
AGATGTTGGG TTAAGTCCCG CAACGAGCGC AACCCTTGAT CTTAGTTGCC AGCATTCAGT  1140
TGGGCACTCT AAGGTGACTG CCGGTGACAA ACCGGAGGAA GGTGGGGATG ACGTCAAATC  1200
ATCATGCCCC TTATGACCTG GGCTACACAC GTGCTACAAT GGGCAGAACA AAGGGCAGCG  1260
AAACCGCGAG GTTAAGCCAA TCCCACAAAT CTGTTCTCAG TTCGGATCGC AGTCTGCAAC  1320
TCGACTGCGT GAAGCTGGAA TCGCTAGTAA TCGCGGATCA CCACGAGAGT GTGAATACGT  1380
TCCCGGGCCT TGTACACACC GCCCGTCACA CCACGAGAGT TTGTAACACC CGAAGTCGGT  1440
GAGGTAACCT TTATGGAGCC AGCCGCCGAA GGTGGGACAG ATGATTGGGG TGAAGTCGTA  1500
ACAAGGTAAC CG                                                    1512
```

FIG. 8F

```
GCCTAACAGT GCGAGTCGGA CGGTAGCACA GAGGAGCTTG CTCTTCGGGT GACGAGTGGC      60
GGACGGGTGA GTAATGTCTG GGGATCTGCC CGATGGAGGG GGATAACCAC TGGAAACGGT     120
GGCTAATACC GCATAATGTC GCAAGACCAA AGTGGGGGAC CTTCGGGCCT CACACCATCG     180
GATGAACCCA GATGGGGATTA GCTAGTAGGT GGGGTAACGG CTCACCTAGG CGACGATCCC    240
TAGCTGGTCT GAGAGGATGA CCAGCCACAC TGGAACTGAG ACACGGTCCA GACTCCTACG     300
GGAGGCAGCA GTGGGGAATA TTGCACAATG GGCGCAAGCC TGATGCAGCC ATGCCGCGTG     360
TATGAAGAAG GCCTTCGGGT TGTAAAGTAC TTTCAnCGGG GAGGAAGGGG ACGAGGTTAA     420
TAACCCCGTT CATTGACGTT ACCCGCAGAA GAAGCACCGG CTAACTCCGT GCCAGCAGCC     480
GCGGTAATAC GGAGGGTGCA AGCGTTAATC GGAATTACTG GGCGTAAAGC GCACGCAGGC     540
GGTCTGTTAA GTCAGATGTG AAATCCCCGG GCTTAACCTG GGAACTGCAT TTGAAACTGG     600
CAGGCTTGAG TCTTGTAGAG GGGGGTAGAA TTCCAGGTGT AGCGGTGAAA TGCGTAGAGA     660
TCTGGAGGAA TACCGGTGGC GAAGGCGGCC CCCTGGACAA AGACTGACGT TCAGTGCGAA     720
AAGCGTGGGG AGCAAACAGG ATTAGATACC CTGGTAGTCC ACGCCGTAAA CGATGTCGAC     780
TTGGAGGCTG TGAGCATGAT TCGTGGCTTC CGGAGCTAAC GCGTTAAGTC GACCGCCTGG     840
GGAGTACGGC CGCAAGGTTA AAATTCAAAT GAATTGACGG GGGCCCGCAC AAGCGGTGGA     900
GCATGTGGTT TAATTCGATG CAACGCGAAG AACCTTACCT GyTCTTGACA TCCACGGAAT     960
TyGCAGAGA TGCCTTAGTG CCTTCGGGAA CCGTGAGACA GGTGCTGCAT GGCTGTCGTC    1020
AGCTCGTGTT GTGAAATGTT GGGTTAAGTC CGCAACCCTT ATCCTTTGTT                1080
GCCAGCGATT CGGTCGGGAA CTCAAAGGAG ACTGCCGGTG ATAAACCGGA GGAAGGTGGG   1140
GATGACGTCA AGTCATCATG GCCCTTACGA GCAGGGCTAC ACACGTGCTA CAATGGCGCA   1200
TACAAAGAGA AGCGACCTCG CGAGAGCAAG CGGACCTCAC AAAGTGCGTC GTAGTCCGGA   1260
TCGGAGTCTG CAACTCGACT CCGTGAAGTC GGAATCGCTA GTAATCGTGG ATCAGAATGC   1320
CACGGTGAAT ACGTTCCCGG GCCTTGTACA CACCGCCCGT CACACCATGG GAGTGGGTTG   1380
CAAAAGAAGT AGGTAGCTTA ACCTTCGGGA GGGCGCTTAC CACTTTGTGA TTCATGACTG   1440
GGGTGAAGTC GTAACAAG                                                   1458
```

```
AGTGCGAGTC GGACGGTAGC ACAGAGAGCT TGCTCTTGGG TGACGAGTGG CGGACGGGTG   60
AGTAATGTCT GGGGATCTGC CCGATAGAGG GGGATAACCA CTGGAAACGG TGGCTAATAC  120
CGCATAACGT CGCAAGACCA AAGAGGGGGA CCTTCGGGCC TCTCACTATC GGATGAACCC  180
AGATGGGATT AGCTAGTAGG CGGGGTAATG GCCCACCTAG GCGACGATCC CTAGCTGGTC  240
TGAGAGGATG ACCAGCCACA CTGGAACTGA GACACGGTCC AGACTCCTAC GGGAGGCAGC  300
AGTGGGGAAT ATTGCACAAT GGGCGCAAGC CTGATGCAGC CATGCCGCGT GTATGAAGAA  360
GGCCCTTCGG TTGTAAAGTA CTTTCAGCGG GAGGAAGGC GATGCGGTTA ATAACCCTGT  420
CGATTGACGT TACCCGCAGA AGAAGCACCG GCTAACTCCG TGCCAGCAGC CGCGGTAATA  480
CGGAGGGTGC AAGCGTTAAT CGGAATTACT GGGCGTAAAG CGCACGCAGG CGGTCTGTTA  540
AGTCAGATGT GAAATCCCCG GGCTTAACCT GGGAACTGCA TTTGAAACTG GCAGGCTTGA  600
GTCTTGTAGA rGGGGGTAGA ATTCCAGGTG TAGCGGTGAA ATGCGTAGAG ATCTGGAGGA  660
ATACCGGTGG CGAAGGCGGC CCCCTGGACA AAGACTGACG CTCAGGTGCG AAAGCGTGGG  720
GAGCAAACAG GATTAGATAC CCTGGTAGTC CACGCCGTAA ACGATGTCGA CTTGGAGTT  780
GTTCCCTTGA GGAGTGGCTT CCGGAGCTAA CGCGTTAAGT CGACCGCCTG GGGAGTACGG  840
CCGCAAGGTT AAAATTCAAA TGAATTGACG GGGGCCCGCA CAAGCGGTGG AGCATGTGGT  900
TTAATTCGAT GCAACGCGAA GAACCTTACC TACTCTTGAC ATCCACGAA TTyGGCAGAG  960
ATGCTTTGGT GCCTTCGGGA ACCCTGAGAC AGTGCTGCA TGGCTCGTCGT CAGCTCGTGT 1020
TGTGAAATGT TGGGTTAAGT CCCGCAACGA GCGCAACCCT TATCCTTTGT TGCCAGCGAT 1080
TCGGTCGGGA ACTCAAAGGA GACTGCCGGT GATAAACCGG AGGAAGGTGG GGATGACGTC 1140
AAGTCATCAT GGCCCTTACG AGTAGGGCTA CACACGTGCT ACAATGGCGC ATACAAAGAG 1200
AAGCGACCTC GCGAGAGCAA GCGGACCTCA CAAAGTGCGT CGTAGTCCGG ATCGGAGTCT 1260
GCAACTCGAC TCCGTGAAGT CGGAATCGCT AGTAATCGTG GATCAGAATG CCACGGTGAA 1320
TACGTTCCCG GGCCTTGTAC ACACCGCCCG TCACACCATG GGAGTGGGTT GCAAAAGAAG 1380
TAGGTAGCTT AACCTTCGGG AGGGCGCTTA CCACTTTGTG ATTCATGACT GGGGTGAAGT 1440
CGTAACAAGT A                                                      1451
```

FIG. 8I

```
AGAGTTTGAT CATGGCTCAG GATGAACGCT GGCGGCGTGC CTAATACATG CAAGTCGAGC    60
GAACTGATTA GAAGCTTGCT TCTATGACGT TAGCGGCGGA CGGGTGAGTA ACACGTGGGC   120
AACCTGCCTG TAAGACTGGG ATAACTTCGG GAAACCGAAG CTAATACCGG ATAGGATCTT   180
CTCCTTCATG GGAGATGATT GAAAGATGGT TTCGGCTATC ACTTACAGAT GGGCCCGCGG   240
TGCATTAGCT AGTTGGTGAG GTAACGGCCC ACCAAGGCAA CGATGCATAG CCGACCTGAG   300
AGGGTGATCG GCCACACTGG GACTGAGACA CGGCCCAGAC TCCTACGGGA GGCAGCAGTA   360
GGGAATCTTC CGCAATGGAC GAAAGTCTGA CGGAGCAACG CCGCGTGAGT GATGAAGGCT   420
TTCGGGTCGT AAAACTCTGT TGTTAGGGAA GAACAAGTAC GAGAGTAACT GCTCGTACCT   480
TGACGGTACC TAACCAGAAA GCCACGGCTA ACTACGTGCC AGCAGCCGCG GTAATACGTA   540
GGTGGCAAGC GTTATCCGGA ATTATTGGGC GTAAAGCGCG CCGCAGGCGG TTTCTTAAGT   600
CTGATGTGAA AGCCCACGGC TCAACCGTGG GArGGTCATT GGAAACTGGG GAACTTGAgT   660
GCAGAAGAGA AAAGCGGAAT TCCACGTGTA GCGGTGAAAT GCGTAGAGAT GTGGAGGAAC   720
ACCAGTGGCG AAGGCGGCTT TTTGGTCTGT AACTGACGCT GAGGCGCGAA AGCGTGGGGA   780
GCAAACAGGA TTAGATACCC TGGTAGTCCA CGCCGTAAAC GATGAGTGCT AAGTGTTAGA   840
GGGTTTCCGC CCTTTAGTGC TGCAGCTAAC GCATTAAGCA CTCCGCCTGG GGAGTACGGT   900
CGCAAGACTG AAACTCAAAG GAATTGACGG GGGCCCGCAC AAGCGGTGGA GCATGTGGTT   960
TAATTCGAAG CAACGCGAAG AACCTTACCA GGTCTTGACA TCCTCTGACA ACTCTAGAGA  1020
TAGAGCtTTC CCCTTCGGGG GACAGAGTGA CAGGTGGTGC ATGGTTGTCG TCAGCTCGTG  1080
TCGTGAGATG TTGGGTTAAG TCCCGCAACG AGCGCAACCC TTGATCTTAG TTGCCAGCAT  1140
TTAGTTGGGC ACTCTAAGGT GACTGCCGGT GACAAACCGG AGGAAGGTGG GGATGACGTC  1200
AAATCATCAT GCCCCTTATG ACCTGGGCTA CACACGTGCT ACAATGGATG GTACAAAGGG  1260
CTGCAAGACC GCGAGGTCAA GCCAATCCCA TAAAACCATT CTCAGTTCGG ATTGTAGGCT  1320
GCAACTCGCC TACATGAAGC TGGAATCGCT AGTAATCGCG GATCAGCATG CCGCGGTGAA  1380
TACGTTCCCG GGCCTTGTAC ACACCGCCCG TCACACCACG AGAGTTTGTA ACACCCGAAG  1440
TCGGTGGAGT AACCGTAAGG AGCTAGCCGC CTAAGGTGGG ACAGATGATT GGGGTGAAGT  1500
CGTAACAAGG TAG                                                    1513
```

```
CGCTGGGCGG CCTGCTTAAC ACnTGCAAGT CGAACGATGA TGCCCAGCTT GCTGGGTGGA   60
TTAGTGGCGA ACGGGTGAGT AACACGTGAG TAACCTGCCC CTGACTCTGG GATAAGCGTT  120
GGAAACGACG TCTAATACTG GATATGATCA CTGGCCGCAT GGTCTGGTGG TGGAAAGATT  180
TTTTGGTTGG GGATGGACTC GCGGCCTATC AGCTTGTTGG TGAGGTAATG GCTCACCAAG  240
GCGACGACGG GTAGCCGGCC TGAGAGGGTG ACCGGCCACA CTGGGACTGA GACACGGCCC  300
AGACTCCTAC GGGAGGCAAC AGTGGGGAAT ATTGCACAAT GGGCGAAAGC CTGATGCAGC  360
AACGCCGCGT GAGGGATGAC GGCCTTCGGG TTGTAAACCT CTTTTAGTAG GGAAGAAGCG  420
AAAGTGACGG TACCTGCAGA AAAAGCACCG GCTAACTACG TGCCAGCAGC CGCGGTAATA  480
CGTAGGGTGC AAGCGTTGTC CGGAATTATT GGGCGTAAAG AGCTCGTAGG CGGTTTGTCG  540
CGTCTGCTGT GAAATCCCGA GGCTCAACCT CGGGCTTGCA GTGGGTACGG GCAGACTAGA  600
GTGCGGTAGG GGAGATTGGA ATTCCTGGTG TAGCGGTGGA ATGCGCAGAT ACCAGGAGGA  660
ACACCGATGG CGAAGGCAGA TCTCTGGGCC GTAACTGACG CTGAGGAGCG AAAGCATGGG  720
GAGCGAACAG GATTAGATAC CCTGGTAGTC CATGCCGTAA ACGTTGGGCG CTAGATGTAG  780
GGACCTTTCC ACGGTTTCTG TGTCGTAGCT AACGCATTAA GCGCCCCGCC TGGGGAGTAC  840
GGCCGCAAGG CTAAAACTCA AAGGAATTGA CGGGGGCCCG CACAAGCGGC GGAGCATGCG  900
GATTAATTCG ATGCAACGCG AAGAACCTTA CCAAGGmTTG ACATACACCG GAAACGGCCA  960
GAGATGGTCG CCCCCTTGTG GTCGGTGTAC AGGTGGTGCA TGGTTGTCGT CAGCTCGTGT 1020
CGTGAGATGT TGGGTTAAGT CCCGCAACGA GCGCAACCCT CGTTCTATGT TGCCAGCGGG 1080
TTATGCCGGG GACTCATAGG AGACTGCCGG GGTCAACTCG GAGGAAGGTG GGGATGACGT 1140
CAAATCATCA TGCCCCTTAT GTCTTGGGCT TCACGCATGC TACAATGGCC GGTACAAAGG 1200
GCTGCGATAC CGTAAGGTGG AGCGAATCCC AAAAAGCCGG TCTCAGTTCG GATTGAGGTC 1260
TGCAACTCGA CCTCATGAAG TCGGAGTCGC TAGTAATCGC AGATCAGCAA CGCTGCGGTG 1320
AATACGTTCC CGGGCCTTGT ACACACCGCC CGTCAAGTCA TGAAAGTCGG TAACACCCGA 1380
AGCCGGTGGC CTAACCCTTG CTAACCCTTG CGGAAGGAGC CGTCGAAGGT GGGATCGGTG 1440
AGTCGTAACA AG                                                     1452
```

FIG. 8J

```
AGAGTTTGAT CATGGCTCAG AACGAACGCT GGCGGCATGC CTAACACATG CAAGTCGAAC    60
GAGATCTTCG GATCTAGTGG CGCACGGGTG CGTAACGCGT gGGAATCTGC cCTTtGGTTC   120
GGAATAaCAG TTGGAAACGA CTGCTAATgA CCGGATGATG ACGTAAGTCC AAAGATTTAT   180
CGCCAGAGGA TkAGCCCGCG TAGGATTAGC tAgTTGGTGT GGTAaGAGCG CACCAAGGCG   240
ACgAtCCTTA GCTGGTCTGA GArGAtGAtC AGCCACACTG GGACTGAGAc ACGGcCCAgA   300
CTCCTACGGG AGGCAGCAGT GGGGAATwTT GGACAATGGG CGAAAGCCTG ATCCAGCAAT   360
GCCGCGTGAG TGATGAAGGC CTTAGGGTTG TAAAGCTCTT TTACCCGGGA TGATAAATGAC  420
AGTACCGGGA GAATAAGCTC CGGCTAACTC CGTGCCAGCA GCCGCGGTAA TACGAGGGA    480
GCTAGCGTTG TTCGGAATTA CTGGGCGTAA AGCGCACGTA GGCGGCTTTG TAAGTTAGAG   540
GTGAAAGCCT GGAGCTCAAC TCCAGAATTG CCTTTAAGAC TGCATCGCTT GAATCCAGGA   600
GAGGTGAGTG GAATTCCGAG TGTAGAGGTG AAATTCGTAG ATATTCGGAA GAACACCAGT   660
GGCGAAGGCG GCTCACTGGA CTGGTATTGA CGCTGAGGTG CGAAAGCGTG GGGAGCAAAC   720
AGGATTAGAT ACCCTGGTAG TCCACGCCGT AAACGATGAT AACTAGCTGT CCGGGACTT    780
GGTCTTTGGG TGGCGCAGCT AACGCATTAA GTTATCCGCC TGGGGAGTAC GGCCGCAAGG   840
TTAAAACTCA AATGAATTGA CGGGGGCCTG CACAAGCGGT GGAGCATGTG GTTTAATTCG   900
AAGCAACGCG CAGAACCTTA CCAGCGTTTG ACATGTCCGG ACGATTTCTG GAGACAGATC   960
TCTTCCCTTC GGGACTGGA ACACAGGTGC TGCATGGCTG TCGTCAGCTC GTGTCGTGAG   1020
ATGTTGGGTT AAGTCCCGCA ACGAGCGCAA CCCTCGCCTT TAGTTACCAT CATTTAGTTG  1080
GGGACTCTAA AGGAACCGCC GGTGATAAGC CGGAGGAAGG TGGGGATGAC GTCAAGTCCT  1140
CATGGCCCTT ACGCGCTGGG CTACACACGT GCTACAATGG CGGTGACAGT GGGCAGCAAA  1200
CTCGCGAGAG TGCGCTAATC TCCAAAAGCC GTCTCAGTTC GGATTGTTCT CTGCAACTCG  1260
AGAGCATGAA GGCGGAATCG CTAGTAATCG CGGATCAGCA TGCCGCGGTG AATACGTTCC  1320
CAGGCCTTGT ACACACCGCC CGTCACACCA TGGGAGTTGG GTTCACCCGA AGGCGTTGCG  1380
CTAACTCAGC ACACACCGCC CGTCACACCA TGGGAGTTGG GTTCACCCGA AGGCGTTGCG  1380
CTAACTCAGC AATGAGAGGC AGGCGACCAC AGGCGACCAC GCGACTGGGG TGAAGTCGTA  1440
ACAAGGTAAC                                                         1450
```

FIG-8K

| m/z | Assignment |
|---|---|
| 447 | $(T-BzOH)^+$ |
| 386 | $(T-H_2O-BzOH-AcOH)^+$ |
| 326 | $(T-BzOH-2AcOH-H_2O)^+$ |
| 308 | $(T-BzOH-2AcOH-2H_2O)^+$ |

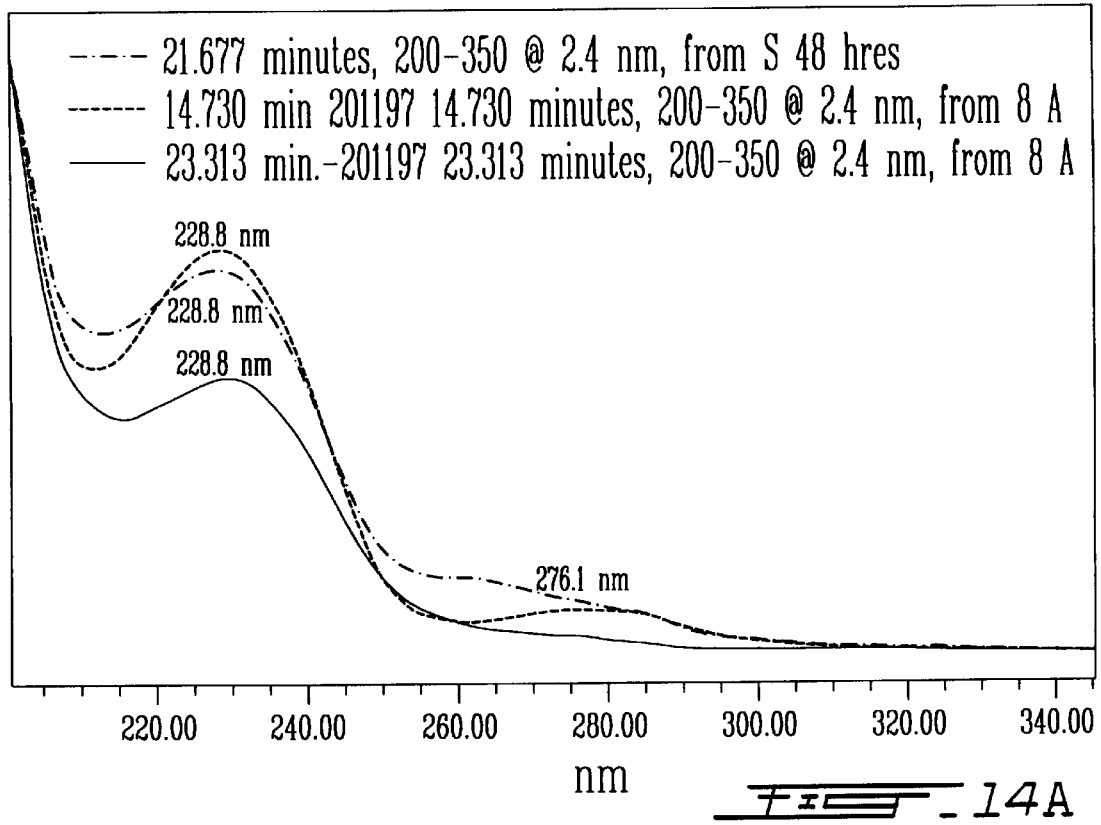
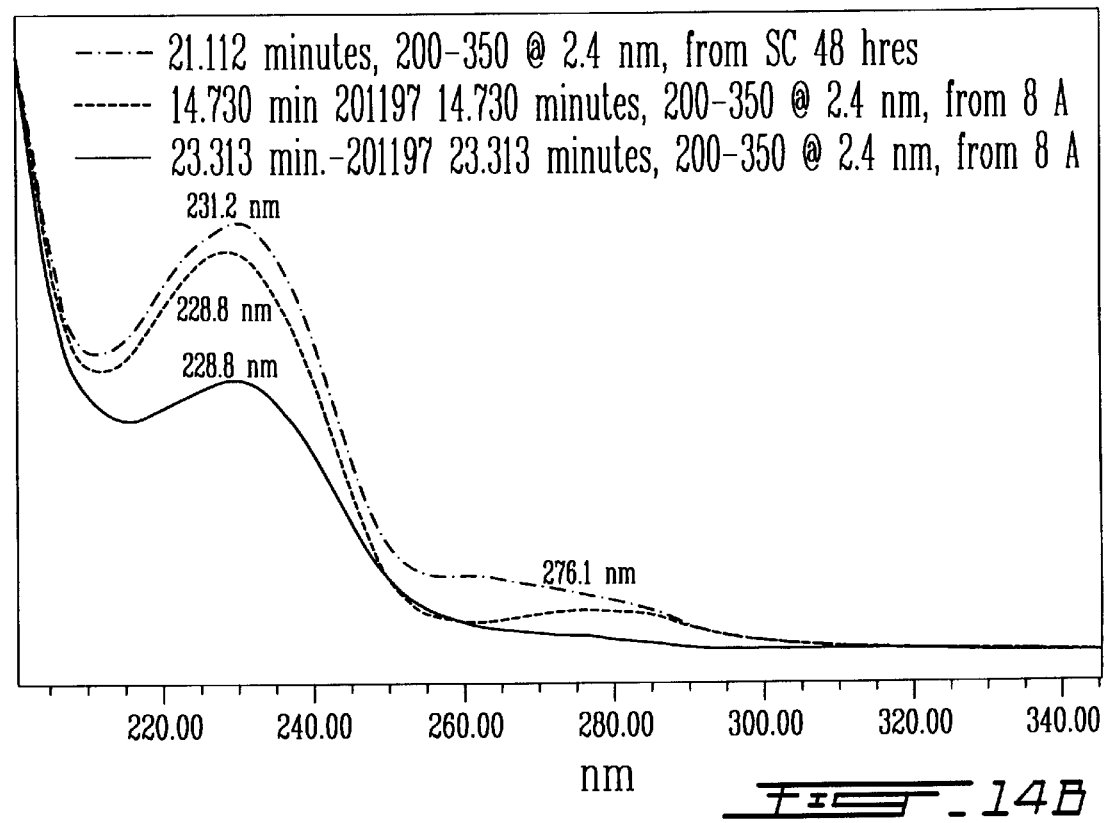

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
      (A) LENGTH: 1556 base pairs
      (B) TYPE: nucleic acid
      (C) STRANDEDNESS: single
      (D) TOPOLOGY: linear (ii) MOLECULE TYPE: rRNA (xi) SEQUENCE DESCRIPTION: SEQ ID NO:1:

```
ATGATTACGC CAAGCTATTT AGGTGACACT ATAGAATACT CAAGCTATGC ATCCAACGCG      60

TTGGGAGCTC TCCCATATGG TCGACCTGCA GGCGGCCGCA CTAGTGATTA GAGTTTGATC     120

CTGGCTCAGA ACGAACGCTG GCGGCATGCC TAACACATGC AAGTCGAACG AGATCTTCGG    180
```

```
ATCTAGTGGC GCACGGGTGC GTAACGCGTG GGAATCTGCC CTTTGGTTCG GAATAACAGT      240

TGGAAACGAC TGCTAATACC GGATGATGAC GTAAGTCCAA AGATTTATCG CCAGAGGATG      300

AGCCCGCGTA GGATTAGCTA GTTGGTGTGG TAAGAGCGCA CCAAGGCGAC GATCCTTAGC      360

TGGTCTGAGA GGATGATCAG CCACACTGGG ACTGAGACAC GGCCCAGACT CCTACGGGAG      420

GCAGCAGTGG GGAATATTGG ACAATGGGCG AAAGCCTGAT CCAGCAATGC CGCGTGAGTT      480

GATGAAAGCC TTAGGTTGTT AAAGCTCTTT TACCCGGGAA TGATAATGAC AGTACCGGGA      540

GAATAAGCTC CGGCTAACTC CGTGCCAGCA GCCGCGGTAA TACGGAAGGA GCTAGCGTTG      600

TTCGGAATTA CTGGGCGTAA AGCGCACGTA GGCGGCTTTG TAAGTTAGAG GTGAAAGCCT      660

GGAGCTCAAC TCCAGAATTG CCTTTAAGAC TGCATCGCTT GAATCCAGGA GAGGTGAGTG      720

GAATTCCGAG TGTAGAGGTG AAATTCGTAG ATATTCGGAA GAACACCAGT GGCGAAGGCG      780

GCTCACTGGA CTGGTATTGA CGCTGAGGTG CGAAAGCGTG GGGAGCAAAC AGGATTAGAT      840

ACCCTGGTAG TCCACGCCGT AAACGATGAT AACTAGCTGT CCGGGACTT GGTCTTTGGG       900

TGGCGCAGCT AACGCATTAA GTTATCCGCC TGGGGAGTAC GGCCGCAAGG TTAAAACTCA      960

AATGAATTGA CGGGGGCCTG CACAAGCGGT GGAGCATGTG GTTTAATTCG AAGCAACGCG     1020

CAGAACCTTA CCAGCGTTTG ACATGTCCGG ACGATTTCTG GAGACAGATC TCTTCCCTTC     1080

GGGGACTGGA ACGCAGGTGC TGCATGGCTG TCGTCAGCTC GTGTCGTGAG ATGTTGGGTT     1140

AAGTCCCGCA ACGAGCGCAA CCCTCGCCTT TAGTTACCAT CATTTAGTTG GGACTCTAA     1200

AGGAACCGCC GGTGATAAGC CGGAGGAAGG TGGGGATGAC GTCAAGTCCT CATGGCCCTT     1260

ACGCGCTGGG CTACACACGT GCTACAATGG CGGTGACAGT GGGCAGCAAA CTCGCGAGAG     1320

TGCGCTAATC TCCAAAAGCC GTCTCAGTTC GGATTGTTCT CTGCAACTCG AGAGCATGAA     1380

GGCGGAATCG CTAGTAATCG CGGATCAGCA TGCCGCGGTG AATACGTTCC CAGGCCTTGT     1440

ACACACCGCC CGTCACACCA TGGGAGTTGG GTTCACCCGA AGGCGTTGCG CTAACTCGTA     1500

AGAGAGGCAG GCGACCACGG TGGGCTTAGC GACTGGGGTG AAGTCGTAAC AAGGTA        1556

(2) INFORMATION FOR SEQ ID NO:2:

(i) SEQUENCE CHARACTERISTICS:
        (A) LENGTH: 1512 base pairs
        (B) TYPE: nucleic acid
        (C) STRANDEDNESS: single
        (D) TOPOLOGY: linear (ii) MOLECULE TYPE: rRNA (xi) SEQUENCE DESCRIPTION: SEQ ID NO:2:

AGAGTTTGAT CATGGCTCAG GATGAACGCT GGCGGCGTGC CTAATACATG CAAGTCGAGC       60

GAATGGATTA AGAGCTTGCT CTTATGAAGT TAGCGGCGGA CGGGTGAGTA ACACGTGGGT      120

AACCTACCCA TAAGACTGGG ATAACTCCGG GAAACCGGGG CTAATACCGG ATAATATTTT      180

GAACTGCATA GTTCGAAATT GAAAGGCGGC TTCGGCTGTC ACTTATGGAT GGACCCGCGT      240

CGCATTAGCT AGTTGGTGAG GTAACGGCTC ACCAAGGCGA CGATGCGTAG CCGACCTGAG      300

AGGGTGATCG GCCACACTGG GACTGAGACA CGGCCCAGAC TCCTACGGGA GGCAGCAGTA      360

GGGAATCTTC CGCAATGGAC GAAAGTCTGA CGGAGCAACG CCGCGTGAGT GATGAAGGCT      420

TTCGGGTCGT AAAACTCTGT TGTTAGGGAA GAACAAGTGC TAGTTGAATA AGCTGGCACC      480

TTGACGGTAC CTAACCAGAA AGCCACGGCT AACTACGTGC CAGCAGCCCG CGGTAATACG      540

TAGGTGGCAA GCGTTATCCG GAATTATTGG GCGTAAAGCG CGCGCAGGTG GTTTCTTAAG      600
```

```
TCTGATGTGA AAGCCCACGG CTCAACCGTG GAGGGTCATT GGAAACTGGG AGACTTGAGT      660

GCAGAAGAGG AAAGTGGAAT TCCATGTGTA GCGGTGAAAT GCGTAGAGAT ATGGAGGAAC      720

ACCAGTGGCG AAGGCGACTT TCTGGTCTGT AACTGACACT GAGGCGCGAA AGCGTGGGGA      780

GCAAACAGGA TTAGATACCC TGGTAGTCCA CGCCGTAAAC GATGAGTGCT AAGTGTTAGA      840

GGGTTTCCGC CCTTTAGTGC TGAAGTTAAC GCATTAAGCA CTCCGCCTGG GGAGTACGGC      900

CGCAAGGCTG AAACTCAAAG GAATTGACGG GGGCCCGCAC AAGCGGTGGA GCATGTGGTT      960

TAATTCGAAG CAACGCGAAG AACCTTACCA GGTCTTGACA TCCTCTGAAA ACTCTAGAGA     1020

TAGAGCTTCT CCTTCGGGAG CAGAGTGACA GGTGGTGCAT GGTTGTCGTC AGCTCGTGTC     1080

GTGAGATGTT GGGTTAAGTC CCGCAACGAG CGCAACCCTT GATCTTAGTT GCCATCATTA     1140

AGTTGGGCAC TCTAAGGTGA CTGCCGGTGA CAAACCGGAG GAAGGTGGGG ATGACGTCAA     1200

ATCATCATGC CCCTTATGAC CTGGGCTACA CACGTGCCAC AATGGACGGT ACAAAGAGCT     1260

GCAAGACCGC GAGGTGGAGC TAATCTCATA AAACCGTTCT CAGTTCGGAT TGTAGGCTGC     1320

AACTCGCCTA CATGAAGCTG GAATCGCTAG TAATCGCGGA TCAGCATGCC GCGGTGAATA     1380

CGTTCCCGGG CCTTGTACAC ACCGCCCGTC ACACCACGAG AGTTTGTAAC ACCCGAAGTC     1440

GGTGGGGTAA CCTTTATGGA GCCAGCCGCC TAAGGTGGGA CAGATGATTG GGGTGAAGTC     1500

GTAACAAGGT AA                                                         1512

(2) INFORMATION FOR SEQ ID NO:3:

(i) SEQUENCE CHARACTERISTICS:
        (A) LENGTH: 554 base pairs
        (B) TYPE: nucleic acid
        (C) STRANDEDNESS: single
        (D) TOPOLOGY: linear (ii) MOLECULE TYPE: rRNA (xi) SEQUENCE DESCRIPTION: SEQ ID NO:3:

TGGTTTAATT CGAAGGGACG CGAAAAACCT TAGGAGGTCT TGACATCCTC TGACAACTCT       60

AGAGATAGAG CGTTCCCCTT CGGGGACAG AGTGACAGGT GGTGCATGGT TGTCGTCAGC      120

TCGTGTCGTG AGATGTTGGG TTAAGTCCCG CAACGAGCGC AACCCTTGAT CTTAGTTGCC      180

AGCATTTAGT TGGGCACTCT AAGGTGACTG CCGGTGACAA ACCGGAGGAA GGTGGGGATG      240

ACGTCAAATC ATCATGCCCC TTATGACCTG GGCTACACAC GTGCTACAAT GGATGGTACA      300

AAGGGCTGCA AGACCGCGAG GTCAAGCCAA TCCCATAAAA CCATTCTCAG TTCGGATTGT      360

AGGCTGCAAC TCGCCTACAT GAAGCTGGAA TCGCTAGTAA TCGCGGATCA GCATGCCGCG      420

GTGAATACGT TCCCGGGCCT TGTACACACC GCCCGTCACA CCACGAGAGT TTGTAACACC      480

CGAAGTCGGT GGAGTAACCG TAAGGAGCTA GCCGCCTAAG GTGGGACAGA TGATTGGGGT      540

GAAGTCGTAA CAAG                                                        554

(2) INFORMATION FOR SEQ ID NO:4:

(i) SEQUENCE CHARACTERISTICS:
        (A) LENGTH: 558 base pairs
        (B) TYPE: nucleic acid
        (C) STRANDEDNESS: single
        (D) TOPOLOGY: linear (ii) MOLECULE TYPE: rRNA (xi) SEQUENCE DESCRIPTION: SEQ ID NO:4:
```

-continued

```
TTACCTTGTT ACGACTTCAC CCCAATCATC TGTCCCACCT TAGGCGGCTA GCTCCTTACG      60

GTTACTCCAC CGACTTCGGG TGTTACAAAC TCTCGTGGTG TGACGGGCGG TGTGTACAAG     120

GCCCGGGAAC GTATTCACCG CGGCATGCTG ATCCGCGATT ACTAGCGATT CCAGCTTCAT     180

GTAGGCGAGT TGCAGCCTAC AATCCGAACT GAGAATGGTT TTATGGGATT GGCTTGACCT     240

CGCGGTCTTG CAGCCCTTTG TACCATCCAT TGTAGCACGT GTGTAGCCCA GGTCATAAGG     300

GGCATGATGA TTTGACGTCA TCCCCACCTT CCTCCGGTTT GTCACCGGCA GTCACCTTAG     360

AGTGCCCAAC TAAATGCTGG CAACTAAGAT CAAGGGTTGC GCTCGTTGCG GGACTTWACC     420

CAACATCTCA CGACACGAGC TGACGACAAC CATGCACCAC CTGTCACTCT GTCCCCCGAA     480

GGGGAACGCT CTATCTCTAG AGTTGTCAGA GGATGTCAAG ACCTCCTAAG GTTTTTCGCG     540

TCCCTTCGAA TTAAACCA                                                   558

(2) INFORMATION FOR SEQ ID NO:5:

(i) SEQUENCE CHARACTERISTICS:
        (A) LENGTH: 626 base pairs
        (B) TYPE: nucleic acid
        (C) STRANDEDNESS: single
        (D) TOPOLOGY: linear (ii) MOLECULE TYPE: rRNA (xi) SEQUENCE DESCRIPTION: SEQ ID NO:5:

TCGGGACGGT CAGCACACGA GGAGCTTGCT CCTTGGGTGA CGAGTGGCGG ACGGGTGAGT      60

AATGTCTGGG GATCTGCCCG ATANAGGGGG ATAACCACTG GAAACGGTGG CTAATACCGC     120

ATAACGTCGC AAGACCAAAG AGGGGGACCT TCGGGCCTCT CACTATCGGA TGAACCCAGA     180

TGGGATTAGC TAGTANGCGG GGTAATGGCC CACCTAGGCG ACGATCCCTA NCTGGTCTGA     240

GAGGATGACC AGCCACACTG GAACTGAGAC ACGGTCCANA CTCCTACGGG AGGCAGCAGT     300

GGGGAATATT GCACAATGGG CGCAAGCCTG ATGCAGCCAT GCCGCGTGTA TGAAGAAGGC     360

CTTCGGGTTG TAAAGTACTT TCAGCGGGGA GGAAGGCGAT GCGGTTAATA ACCCTGTCGA     420

TTGACGTTCC CCGCANGAAG AAGCACCGGC TAACTCCGTG CCAGCAGCCG CGGTAATACC     480

GGAGGGTGCA AGCGTTAATC CGGAATTACT GGGCGTAAAG CGCACGCAGG CGGTCTGTTA     540

AGTCAGATGT GAAATCCCCG GGCTTAACCT GGGGAACTGC ATTTGAAACT GGCAGGCTTN     600

ANTCTTGTCC AGGGGGGTAG AATTCC                                         626

(2) INFORMATION FOR SEQ ID NO:6:

(i) SEQUENCE CHARACTERISTICS:
        (A) LENGTH: 574 base pairs
        (B) TYPE: nucleic acid
        (C) STRANDEDNESS: single
        (D) TOPOLOGY: linear (ii) MOLECULE TYPE: rRNA (xi) SEQUENCE DESCRIPTION: SEQ ID NO:6:

GCACAAGCGG TGGAGCATGT GGTTTAATTC GATGCAACGC GAAGAACCTT ACCTACTCTT      60

GACATCCAGC GAACTTGCCA GAGATGGATT GGTGCCTTCG GGAACGCTGA GACAGGTGCT     120

GCATGGCTGT CGTCAGCTCG TGTTGTGAAA TGTTGGGTTA AGTCCCGCAA CGAGCGCAAC     180

CCTTATCCTT TGTTGCCAGC GATTCGGTCG GGAACTCAAA GGAGACTGCC GGTGATAAAC     240

CGGAGGAAGG TGGGGATGAC GTCAAGTCAT CATGGCCCTT ACGAGTAGGG CTACACACGT     300

GCTACAATGG CGCATACAAA GAGAAGCGAC CTCGCGAGAG CAAGCGGACC TCACAAAGTG     360
```

```
CGTCGTAGTC CGGATCGGAG TCTGCAACTC GACTCCGTGA AGTCGGAATC GCTAGTAATC      420

GTGGATCAGA ATGCCACGGT GAATACGTTC CCGGGCCTTG TACACACCGC CCGTCACACC      480

ATGGGAGTGG GTTGCAAAAG AAGTAGGTAG CTTAACCTTC GGGAGGGCGC TTACCACTTT      540

GTGATTCATG ACTGGGGTGA AGTCGTAACA AGTA                                  574

(2) INFORMATION FOR SEQ ID NO:7:

(i) SEQUENCE CHARACTERISTICS:
        (A) LENGTH: 572 base pairs
        (B) TYPE: nucleic acid
        (C) STRANDEDNESS: single
        (D) TOPOLOGY: linear (ii) MOLECULE TYPE: rRNA (xi) SEQUENCE DESCRIPTION: SEQ ID NO:7:

GCACAAGCGG TGGAGCATGT GGTTTAATTC GAAGCAACGC GAAGAACCTT ACCAGGTCTT       60

GACATCCTCT GAAAACCCTA GAGATAGGGC TTCTCCTTCG GGAGCAGAGT GACAGGTGGT      120

GCATGGTTGT CGTCAGCTCG TGTCGTGAGA TGTTGGGTTA AGTCCCGCAA CGAGCGCAAC      180

CCTTGATCTT AGTTGCCATC ATTAAGTTGG GCACTCTAAG GTGACTGCCG GTGACAAACC      240

GGAGGAAGGT GGGGATGACG TCAAATCATC ATGCCCCTTA TGACCTGGGC TACACACGTG      300

CTACAATGGA CGGTACAAAG AGCTGCAAGA CCGCGAGGTG GAGCTAATCT CATAAAACCG      360

TTCTCAGTTC GGATTGTAGG CTGCAACTCG CCTACATGAA GCTGGAATCG CTAGTAATCG      420

CGGATCAGCA TGCCGCGGTG AATACGTTCC CGGGCCTTGT ACACACCGCC CGTCACACCA      480

CGAGAGTTTG TAACACCCGA AGTCGGTGGG GTAACCTTTT TGGAGCCAGC CGCCTAAGGT      540

GGGACAGATG ATTGGGGTGA AGTCGTAACA AG                                   572

(2) INFORMATION FOR SEQ ID NO:8:

(i) SEQUENCE CHARACTERISTICS:
        (A) LENGTH: 567 base pairs
        (B) TYPE: nucleic acid
        (C) STRANDEDNESS: single
        (D) TOPOLOGY: linear (ii) MOLECULE TYPE: rRNA (xi) SEQUENCE DESCRIPTION: SEQ ID NO:8:

CAAGCGGTGG AGCATGTGGT TTAATTCGAA GCAACGCGAA GAACCTTACC AGGTCTTGAC       60

ATCCTCTGAC AATCCTAGAG ATAGGACGTC CCCTTCGGGG GCAGAGTGAC AGGTGGTGCA      120

TGGTTGTCGT CAGCTCGTGT CGTGAGATGT TGGGTTAAGT CCCGCAACGA GCGCAACCCT      180

TGATCTTAGT TGCCAGCATT CAGTTGGGCA CTCTAAGGTG ACTGCCGGTG ACAAACCGGA      240

GGAAGGTGGG GATGACGTCA AATCATCATG CCCCTTATGA CCTGGGCTAC ACACGTGCTA      300

CAATGGACAG AACAAAGGGC AGCGAAACCG CGAGGTTAAG CCAATCCCAC AAATCTGTTC      360

TCAGTTCGGA TCGCAGTCTG CAACTCGACT GCGTGAAGCT GGAATCGCTA GTAATCGCGG      420

ATCAGCATGC CGCGGTGAAT ACGTTCCCGG GCCTTGTACA CACCGCCCGT CACACCACGA      480

GAGTTTGTAA CACCCGAAGT CGGTGAGGTA ACCTTTATGG AGCCAGCCGC CGAAGGTGGG      540

ACAGATGATT GGGGTGAAGT CGTAACA                                         567

(2) INFORMATION FOR SEQ ID NO:9:

(i) SEQUENCE CHARACTERISTICS:
```

(A) LENGTH: 711 base pairs
(B) TYPE: nucleic acid
(C) STRANDEDNESS: single
(D) TOPOLOGY: linear (ii) MOLECULE TYPE: rRNA (xi) SEQUENCE DESCRIPTION: SEQ ID NO:9:

```
GCCTAACAGT GCGAGTCGGA CGGTAGCACA GAGGAGCTTG CTCTTCGGGT GACGAGTGGC     60
GGACGGGTGA GTAATGTCTG GGATCTGCC CGATGGAGGG GGATAACCAC TGGAAACGGT    120
GGCTAATACC GCATAATGTC GCAAGACCAA AGTGGGGGAC CTTCGGGCCT CACACCATCG    180
GATGAACCCA GATGGGATTA GCTAGTAGGT GGGGTAACGG CTCACCTAGG CGACGATCCC    240
TAGCTGGTCT GAGAGGATGA CCAGCCACAC TGGAACTGAG ACACGGTCCA GACTCCTACG    300
GGAGGCAGCA GTGGGGAATA TTGCACAATG GGCGCAAGCC TGATGCAGCC ATGCCGCGTG    360
TATGAAGAAG GCCTTCGGGT TGTAAAGTAC TTTCANCGGG GAGGAAGGGG ACGAGGTTAA    420
TAACCCCGTT CATTGACGTT ACCCGCAGAA GAAGCACCGG CTAACTCCGT GCCAGCAGCC    480
GCGGTAATAC GGAGGGTGCA AGCGTTAATC GGAATTACTG GGCGTAAAGC GCACGCAGGC    540
GGTCTGTTAA GTCAGATGTG AAATCCCCGG GCTTAACCTG GGAACTGCAT TTGAAACTGG    600
CAGGCTTGAG TCTTGTAGAG GGGGGTAGAA TTCCAGGTGT AGCGGTGAAA TGCCGTAGAG    660
ATCTGGAGGA ATACCGGTGG CGAAGGCGGC CCCCCTGGAC AAAGACTGAC C            711
```

(2) INFORMATION FOR SEQ ID NO:10:

(i) SEQUENCE CHARACTERISTICS:
(A) LENGTH: 572 base pairs
(B) TYPE: nucleic acid
(C) STRANDEDNESS: single
(D) TOPOLOGY: linear (ii) MOLECULE TYPE: rRNA (xi) SEQUENCE DESCRIPTION: SEQ ID NO:10:

```
GCACAAGCGG TGGAGCATGT GGTTTAATTC GATGCAACGC GAAGAACCTT ACCTGCTCTT     60
GACATCCACG GAATTCGGCA GAGATGCCTT AGTGCCTTCG GGAACCGTGA GACAGGTGCT    120
GCATGGCTGT CGTCAGCTCG TGTTGTGAAA TGTTGGGTTA AGTCCCGCAA CGAGCGCAAC    180
CCTTATCCTT TGTTGCCAGC GATTCGGTCG GGAACTCAAA GGAGACTGCC GGTGATAAAC    240
CGGAGGAAGG TGGGGATGAC GTCAAGTCAT CATGGCCCTT ACGAGCAGGG CTACACACGT    300
GCTACAATGG CGCATACAAA GAGAAGCGAC CTCGCGAGAG CAAGCGGACC TCACAAAGTG    360
CGTCGTAGTC CGGATCGGAG TCTGCAACTC GACTCCGTGA AGTCGGAATC GCTAGTAATC    420
GTGGATCAGA ATGCCACGGT GAATACGTTC CCGGGCCTTG TACACACCGC CCGTCACACC    480
ATGGGAGTGG GTTGCAAAAG AAGTAGGTAG CTTAACCTTC GGGAGGGCGC TTACCACTTT    540
GTGATTCATG ACTGGGGTGA AGTCGTAACA AG                                  572
```

(2) INFORMATION FOR SEQ ID NO:11:

(i) SEQUENCE CHARACTERISTICS:
(A) LENGTH: 704 base pairs
(B) TYPE: nucleic acid
(C) STRANDEDNESS: single
(D) TOPOLOGY: linear (ii) MOLECULE TYPE: rRNA (xi) SEQUENCE DESCRIPTION: SEQ ID NO:11:

-continued

```
AGTGCGAGTC GGACGGTAGC ACAGAGAGCT TGCTCTTGGG TGACGAGTGG CGGACGGGTG    60

AGTAATGTCT GGGGATCTGC CCGATAGAGG GGGATAACCA CTGGAAACGG TGGCTAATAC   120

CGCATAACGT CGCAAGACCA AAGAGGGGGA CCTTCGGGCC TCTCACTATC GGATGAACCC   180

AGATGGGATT AGCTAGTAGG CGGGGTAATG GCCCACCTAG GCGACGATCC CTAGCTGGTC   240

TGAGAGGATG ACCAGCCACA CTGGAACTGA GACACGGTCC AGACTCCTAC GGGAGGCAGC   300

AGTGGGGAAT ATTGCACAAT GGGCGCAAGC CTGATGCAGC CATGCCGCGT GTATGAAGAA   360

GGCCTTCGGG TTGTAAAGTA CTTTCAGCGG GGAGGAAGGC GATGCGGTTA ATAACCCTGT   420

CGATTGACGT TACCCGCAGA AGAAGCACCG GCTAACTCCG TGCCAGCAGC CGCGGTAATA   480

CGGAGGGTGC AAGCGTTAAT CGGAATTACT GGGCGTAAAG CGCACGCAGG CGGTCTGTTA   540

AGTCAGATGT GAAATCCCCG GGCTTAACCT GGGAACTGCA TTTGAAACTG GCAGGCTTGA   600

GTCTTGTAGA AGGGGGTAGA ATTCCAGGTG TAGCGGTGAA ATGCGTAGAG ATCTGGAGGA   660

ATACCGGTGG CGAAGGCGGC CCCCTGGACA AAGACTGACG CTCA                   704
```

(2) INFORMATION FOR SEQ ID NO:12:

(i) SEQUENCE CHARACTERISTICS:
        (A) LENGTH: 574 base pairs
        (B) TYPE: nucleic acid
        (C) STRANDEDNESS: single
        (D) TOPOLOGY: linear (ii) MOLECULE TYPE: rRNA (xi) SEQUENCE DESCRIPTION: SEQ ID NO:12:

```
GCACAAGCGG TGGAGCATGT GGTTTAATTC GATGCAACGC GAAGAACCTT ACCTACTCTT    60

GACATCCACC GAACTTAGCA GAGATGCTTT GGTGCCTTCG GGAACCCTGA GACAGGTGCT   120

GCATGGCTGT CGTCAGCTCG TGTTGTGAAA TGTTGGGTTA AGTCCCGCAA CGAGCGCAAC   180

CCTTATCCTT TGTTGCCAGC GATTCGGTCG GGAACTCAAA GGAGACTGCC GGTGATAAAC   240

CGGAGGAAGG TGGGGATGAC GTCAAGTCAT CATGGCCCTT ACGAGTAGGG CTACACACGT   300

GCTACAATGG CGCATACAAA GAGAAGCGAC CTCGCGAGAG CAAGCGGACC TCACAAAGTG   360

CGTCGTAGTC CGGATCGGAG TCTGCAACTC GACTCCGTGA AGTCGGAATC GCTAGTAATC   420

GTGGATCAGA ATGCCACGGT GAATACGTTC CCGGGCCTTG TACACACCGC CCGTCACACC   480

ATGGGAGTGG GTTGCAAAAG AAGTAGGTAG CTTAACCTTC GGGAGGGCGC TTACCACTTT   540

GTGATTCATG ACTGGGGTGA AGTCGTAACA AGTA                             574
```

(2) INFORMATION FOR SEQ ID NO:13:

(i) SEQUENCE CHARACTERISTICS:
        (A) LENGTH: 573 base pairs
        (B) TYPE: nucleic acid
        (C) STRANDEDNESS: single
        (D) TOPOLOGY: linear (ii) MOLECULE TYPE: rRNA (xi) SEQUENCE DESCRIPTION: SEQ ID NO:13:

```
GCACAAGCGG TGGAGCATGT GGTTTAATTC GAAGGAACGC GAAGAACCTT ACCAGGTCTT    60

GACATCCTCT GACAACTCTA GAGATAGAGC GTTCCCCTTC GGGGGACAGA GTGACAGGTG   120

GTGCATGGTT GTCGTCAGCT CGTGTCGTGA GATGTTGGGT TAAGTCCCGC AACGAGCGCA   180

ACCCTTGATC TTAGTTGCCA GCATTTAGTT GGGCACTCTA AGGTGACTGC CGGTGACAAA   240

CCGGAGGAAG GTGGGGATGA CGTCAAATCA TCATGCCCCT TATGACCTGG GCTACACACG   300
```

```
TGCTACAATG GATGGTACAA AGGGCTGCAA GACCGCGAGG TCAAGCCAAT CCCATAAAAC    360

CATTCTCAGT TCGGATTGTA GGCTGCAACT CGCCTACATG AAGCTGGAAT CGCTAGTAAT    420

CGCGGATCAG CATGCCGCGG TGAATACGTT CCCGGGCCTT GTACACACCG CCCGTCACAC    480

CACGAGAGTT TGTAACACCC GAAGTCGGTG GAGTAACCGT AAGGAGCTAG CCGCCTAAGG    540

TGGGACAGAT GATTGGGGTG AAGTCGTAAC AAG                                 573
```

(2) INFORMATION FOR SEQ ID NO:14:

(i) SEQUENCE CHARACTERISTICS:
        (A) LENGTH: 759 base pairs
        (B) TYPE: nucleic acid
        (C) STRANDEDNESS: single
        (D) TOPOLOGY: linear (ii) MOLECULE TYPE: rRNA (xi) SEQUENCE DESCRIPTION: SEQ ID NO:14:

```
CGCTGGGCGG CCTGCTTAAC ACNTGCAAGT CGAACGATGA TGCCCAGCTT GCTGGGTGGA     60

TTAGTGGCGA ACGGGTGAGT AACACGTGAG TAACCTGCCC CTGACTCTGG GATAAGCGTT    120

GGAAACGACG TCTAATACTG GATATGATCA CTGGCCGCAT GGTCTGGTGG TGGAAAGATT    180

TTTTGGTTGG GGATGGACTC GCGGCCTATC AGCTTGTTGG TGAGGTAATG GCTCACCAAG    240

GCGACGACGG GTAGCCGGCC TGAGAGGGTG ACCGGCCACA CTGGGACTGA GACACGGCCC    300

AGACTCCTAC GGGAGGCAAC AGTGGGGAAT ATTGCACAAT GGGCGAAAGC CTGATGCAGC    360

AACGCCGCGT GAGGGATGAC GGCCTTCGGG TTGTAAACCT CTTTTAGTAG GGAAGAAGCG    420

AAAGTGACGG TACCTGCAGA AAAAGCACCG GCTAACTACG TGCCAGCAGC CGCGGTAATA    480

CGTAGGGTGC AAGCGTTGTC CGGAATTATT GGGCGTAAAG AGCTCGTAGG CGGTTTGTCG    540

CGTCTGCTGT GAAATCCCGA GGCTCAACCT CGGGCTTGCA GTGGGTACGG GCAGACTAGA    600

GTGCGGTAGG GGAGATTGGA ATTCCTGGTG TAGCGGTGGA ATGCGCAGAT ACCAGGAGGA    660

ACACCGATGG CGAAGGCAGA TCTCTGGGCC GTAACTGACG CTGAGGAGCG AAAGCATGGG    720

GAGCGAACAG GATTAGATAC CCTGGTAGTC CATGCCGTA                          759
```

(2) INFORMATION FOR SEQ ID NO:15:

(i) SEQUENCE CHARACTERISTICS:
        (A) LENGTH: 544 base pairs
        (B) TYPE: nucleic acid
        (C) STRANDEDNESS: single
        (D) TOPOLOGY: linear (ii) MOLECULE TYPE: rRNA (xi) SEQUENCE DESCRIPTION: SEQ ID NO:15:

```
TCGAGGCAAC GCGAAGAACT TACCAAGGAT TGACATACAC CGGAGACGGC CAGAGATGGT     60

CGCCCCCTTG TGGTCGGTGT ACAGGTGGTG CATGGTTGTC GTCAGCTCGT GTCGTGAGAT    120

GTTGGGTTAA GTCCCGCAAC GAGCGCAACC CTCGTTCTAT GTTGCCAGCG GGTTATGCCG    180

GGGACTCATA GGAGACTGCC GGGGTCAACT CGGAGGAAGG TGGGGATGAC GTCAAATCAT    240

CATGCCCCTT ATGTCTTGGG CTTCACGCAT GCTACAATGG CCGGTACAAA GGGCTGCGAT    300

ACCGTAAGGT GGAGCGAATC CCAAAAAGCC GGTCTCAGTT CGGATTGAGG TCTGCAACTC    360

GACCTCATGA AGTCGGAGTC GCTAGTAATC GCAGATCAGC AACGCTGCGG TGAATACGTT    420

CCCGGGCCTT GTACACACCG CCCGTCAAGT CATGAAAGTC GGTAACACCC GAAGCCGGTG    480
```

-continued

```
GCCTAACCCT TGTGGAAGGA GCCGTCGAAG GTGGGATCGG TGATTAGGAC TAAGTCGTAA      540

CAAG                                                                  544

(2) INFORMATION FOR SEQ ID NO:16:

(i) SEQUENCE CHARACTERISTICS:
        (A) LENGTH: 569 base pairs
        (B) TYPE: nucleic acid
        (C) STRANDEDNESS: single
        (D) TOPOLOGY: linear (ii) MOLECULE TYPE: rRNA (xi) SEQUENCE DESCRIPTION: SEQ ID NO:16:

GCACAAGCGG TGGAGCATGT GGTTTAATTC GAAGCAACGC GCAGAACCTT ACCAGCGTTT       60

GACATGTCCG GACGATTTCT GGAGACAGAT CTCTTCCCTT CGGGGACTGG AACACAGGTG      120

CTGCATGGCT GTCGTCAGCT CGTGTCGTGA GATGTTGGGT TAAGTCCCGC AACGAGCGCA      180

ACCCTCGCCT TTAGTTACCA TCATTTAGTT GGGGACTCTA AAGGAACCGC CGGTGATAAG      240

CCGGAGGAAG GTGGGGATGA CGTCAAGTCC TCATGGCCCT TACGCGCTGG GCTACACACG      300

TGCTACAATG GCGGTGACAG TGGGCAGCAA ACTCGCGAGA GTGCGCTAAT CTCCAAAAGC      360

CGTCTCAGTT CGGATTGTTC TCTGCAACTC GAGAGCATGA AGGCGGAATC GCTAGTAATC      420

GCGGATCAGC ATGCCGCGGT GAATACGTTC CCAGGCCTTG TACACACCGC CCGTCACACC      480

ATGGGAGTTG GGTTCACCCG AAGGCGTTGC GCTAACTCAG CAATGAGAGG CAGGCGACCA      540

CGGTGGGCTT AGCGACTGGG GTGAAGTCG                                       569

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

AGAGTTTGAT CMTGGCTCAG                                                   20

(2) INFORMATION FOR SEQ ID NO:18:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

TACGGYTACC TTGTTACGAC TT                                                22
```

BACTERIAL MASS PRODUCTION OF TAXANES AND PACLITAXEL

BACKGROUND OF THE INVENTION (a) Field of the invention

The present invention relates to the production of paclitaxel and derivatives thereof (such as related taxanes) using a plurality of different bacteria isolated from different species of Taxus, and also to a novel taxane. There are disclosed methods for the isolation of these bacteria and the screening tests that were used to provide evidence that paclitaxel and taxanes were produced by said bacteria. There are also disclosed methods for the biotransformation of pro-taxanes by said bacteria.

(b) Description of prior art

Paclitaxel, also referred to as Taxol™, has been first identified in 1971 by Wani and collaborators (Wani MC et al., 1971 *J. Am. Chem. Soc.,* 93: 2325–2327) following a screening program of plant extracts of the National Cancer Institute. This complex diterpene showed cytotoxic activity against several types of tumors and is presently used in the treatment of some cancers such as ovarian and breast cancers. Clinical studies suggest that Taxol™ could eventually be used in the treatment of over 70% of human cancers.

Paclitaxel differs from other cytotoxic drugs by its unique mechanism of action. It interferes with cell division by manipulating the molecular regulation of the cell cycle. Paclitaxel binds to tubulin, the major structural component of microtubules that are present in all eukaryotic cells. Unlike other antimitotic agents such as vinca alkaloids and colcichine, which inhibit the polymerization of tubulin, paclitaxel promotes this assembly of tubulin and stabilizes the resulting microtubules. This event leads to the interruption of cell division, and ultimately to cell death.

The major obstacle in the use of paclitaxel as an anticancer treatment is its supply. It was originally isolated from the bark and leaves of yew trees such as *Taxus brevifolia, T. baccata, T. cuspidata* or, *T. canadensis*. The low yield of the isolation of paclitaxel (0.016 g %) and the limited availability of the trees have forced the scientific and industrial community to find alternative ways of producing paclitaxel.

The antitumor property of taxoid compounds has also lead to the generation of new anticancer drugs derived from taxanes. Taxotere™ (sold by Rhône-Poulenc Rorer), which is produced from 10-deacetylbaccatin III by hemisynthesis, is currently used in the treatment of ovarian and breast cancers. Furthermore, Abbott Laboratories is conducting clinical trials with a drug derived from 9-dihydro-13-acetyl baccatin III, a natural precursor specific to *Taxus canadensis*. The increasing demand for taxanes highlights the urgent need for renewable and economical processes that would not endanger plant species.

Presently, industrials are producing paclitaxel through hemisynthesis from baccatin III, a natural precursor of paclitaxel. However, this process still relies on a plant substance that must be extracted from yew trees. The first complete chemical synthesis of paclitaxel has been achieved in 1994 by Nicolaou et al. (1994, *Nature,* 367:630–634). This is a multistep process and the overall yield has made this approach non economically feasible.

Plant cell culture of Taxus species is another approach explored by many groups (Yukimune et al., 1996, *Nature Biotechnology,* 14:1129–1132; Srinivasan et al., 1995, *Biotechnology and Bioengineering,* 47:666–676). Somehow, this process is limited by the amount of paclitaxel that can be produced, the length of incubation time required to obtain significant yields, and the application of plant cell culture to the large volumes required by the industry.

In U.S. Pat. No. 5,322,779, in the names of Gary A. Strobel et al. disclosed a fungus isolated from the bark of a sample of *Taxus brevifolia* which is able to synthetize paclitaxel at a level of 24–50 ng/l after a period of incubation of 3 weeks. Later, Strobel et al. (1996, *Microbiology,* 142:435–440) reported another fungus, *Pestalotiopsis microspora,* isolated from the inner bark of *Taxus wallachiana* that can produced up to 55 µg/l of paclitaxel within 5 weeks. Somehow, the long periods of incubation and the large volumes required to extract significant amounts of paclitaxel reduce the profitability of the process.

In U.S. Pat. No. 5,561,055 (issued on Oct. 1, 1996 in the names of Michel Pagé et al., the Applicant), there is disclosed one bacterium, which was referred to as *Erwinia taxi,* for the production of paclitaxel. Since then, this bacteria has been characterized as *Sphingomonas taxi*. This bacterium was isolated from *Taxus canadensis*. It would be highly desirable to be provided with other bacteria having highly diverse metabolic capacities isolated from different species of Taxus for the production of paclitaxel and related taxanes at higher yields.

It would also be highly desirable to be provided with widely different bacteria for the mass production of various different bacterial taxanes.

As mentioned in International Patent Application published under number WO97/16200, biotransformation process may be used for the generation of new taxanes molecules that lead to new therapeutic drugs. It would also be highly desirable to be provided with new strains of microorganisms able to biotransform taxanes compounds for use as therapeutic agents or to be modified by hemisynthesis.

Genetic manipulations of bacteria can increase the activity or the production of certain proteins. It would also be highly desirable to be provided with mutant of our original isolates that could produce and biotransform taxanes at higher levels.

SUMMARY OF THE INVENTION

One aim of the present invention is to provide a plurality of bacteria for the mass production of taxanes and paclitaxel.

Another aim of the present invention is to provide a method for bacterial mass production of taxanes and paclitaxel which overcomes all the drawbacks of the prior art.

Another aim of the present invention is to pro- vide a novel process for the production of taxanes and paclitaxel. The industrial application of this process would provide alternative renewable sources of taxoids compounds for the pharmaceutical industry.

Another aim of the present invention is to provide a biotransformation process in which plant-derived taxanes are converted into substances that may be useful for the production of other therapeutic compounds.

In accordance with the present invention there is provided a method to obtain biologically pure cultures of bacteria isolated from Taxus, wherein said bacteria produce de novo taxanes and paclitaxel at a concentration of about 1 to 25 µg/L, wherein said bacteria are isolated from the inner surfaces of different species of Taxus including without limitations *Taxus canadensis, T. brevifolia, T. hunnewelliana, T. baccata,* and *T. cuspidata*.

In addition, said bacteria are capable of producing biotransformed taxanes wherein pro-taxanes are added to their culture medium.

Such biologically pure cultures of bacteria of the present invention include, without limitation, bacteria of the genus selected from the group consisting of Sphingomonas, Bacillus, Pantoea, and Curtobacterium.

In accordance with the present invention, the bacteria include, without limitation, *Bacillus cereus* ssp. *taxi, Bacillus megaterium* ssp. *taxi,* Pantoea sp. BCM 1, Pantoea sp. BCM 2, Pantoea sp. BCM 3, *Bacillus cereus* ssp. BCM 4, *Bacillus subtilis* ssp. *taxi, Bacillus megaterium* ssp. BCM 9 or Curtobacterium sp. BCM 5.

In accordance with the present invention there is also provided a method of bacterial mass production of taxanes and paclitaxel thereof which comprises the steps of:

a) culturing the bacteria of the present invention in a growth-supporting nutrient medium capable of promoting growth and reproduction of said bacteria, and wherein said culturing is effected for a time sufficient to allow production of taxanes and paclitaxel; and b) isolating said produced taxanes and paclitaxel from said bacteria or culturing medium of step a).

In accordance with the present invention there is also provided a process for improving taxanes and paclitaxel production of taxanes and paclitaxel producing bacteria comprising the steps of:

a) culturing bacteria in the presence of a mutagenic agent for a period of time sufficient to allow mutagenesis;

b) selecting said mutants by a change of the phenotype which results in an increased production of taxanes and paclitaxel.

The mutagenic agent may be a chemical agent, such as daunorubicin and nitrosoguanidine.

The mutagenic agent may be a physical agent, such as gamma radiation or ultraviolet.

The mutagenic agent may be a biological agent, such as a transposon.

In accordance with the present invention, the mutated bacteria include, without limitation, *Sphingomonas taxi* D200 or *Sphingomonas taxi* D201.

In accordance with the present invention there is also provided a method of bacterial biotransformation of taxanes and paclitaxel thereof which comprises the steps of:

a) incubating the bacteria of the present invention in a growth-supporting nutrient medium capable of promoting growth and reproduction of said bacteria, and wherein said incubation is effected in the presence of pro-taxanes for a time sufficient to allow production of taxanes and paclitaxel; and b) isolating said produced taxanes and paclitaxel thereof from said culturing medium of step a).

In accordance with the present invention, there is also provided a process for improving biotransformation of pro-taxanes into taxanes and paclitaxel by taxanes and paclitaxel-producing bacteria comprising the steps of:

a) culturing bacteria in the presence of a mutagenic agent for a time sufficient to allow mutagenesis; and b) selecting said mutants by a change of the phenotype which results in an increased biotransformation of pro-taxanes into taxanes and paclitaxel.

In accordance with the present invention there is also provided a method of bacterial biotransformation of pro-taxanes into taxanes and paclitaxel thereof which comprises the steps of:

a) incubating the mutated bacteria of the present invention in a nutrient medium, and wherein said incubation is effected in the presence of pro-taxanes for a time sufficient to allow production of taxanes and paclitaxel; and b) isolating said produced taxanes and paclitaxel thereof from said culturing medium of step a).

In accordance with the present invention there is also provided a novel bacterial taxane having a characteristic ultraviolet spectrum in HPLC as shown in FIG. 9B, Electrospray Ionization (EI) spectrum as shown in FIG. 10A, and characteristic fragments as shown in FIG. 10B.

This novel bacteria-derived taxane of the present invention is produced by at least two species of Bacillus (*B. cereus* ssp. *taxi* and *B. megaterium* ssp. *taxi*).

For the purpose of the present invention the following terms are defined below.

The term "taxanes and paclitaxel" is intended to mean any paclitaxel derivatives or precursor which have retained or not the taxol-associated cytotoxic biological activity or are thought to be precursors in the synthesis of paclitaxel. Such taxanes and paclitaxel may be selected from the group consisting of all the diterpenes isolated from any Taxus species. The production of all taxanes by bacteria, whether pharmacologically active or inactive, is contemplated within the scope of the present invention. Taxanes that are produced by the bacteria of the present invention may be as such found in Taxus plant species or may differs from the ones found in Taxus plant species.

Exemplary taxanes which may be produced by the bacteria of the present invention include but are not limited to those of the following Formula I:

I 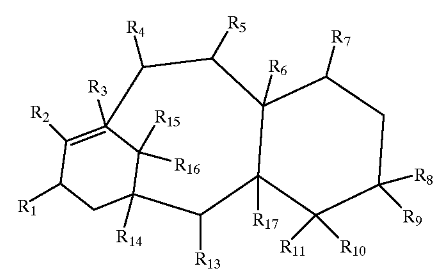 wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$ are defined in Table 1 below.

However, since bacteria have highly diverse metabolic capacities the taxanes and paclitaxel must only correspond to Formula I, whatever is the nature of $R_1$ to $R_{17}$ substituants.

The term "pro-taxanes" used in accordance with the present invention is intended to mean any precursors of any taxanes in the biosynthesis pathway of paclitaxel in plant, fungi and bacteria, including, without limitation, 10-deacetylbaccatin III, baccatin III, cephalomannine, taxinines, taxuspines, taxusin, 7-xylosyl taxol, 7-epi-10-deacetyl taxol, 10-deacetyl taxol, paclitaxel, 7-epitaxol, taxadiene, geranyl-geranyl-pyrophosphate (GGPP) and farnesyl-pyrophosphate.

Exemplary pro-taxanes which may be biotransformed by the bacteria of the present invention include but are not limited to those of the preceding formula I where $R_1$, $R_2$, $R_3$, $R_4$, $R_5$, $R_6$, $R_7$, $R_8$, $R_9$, $R_{11}$, $R_{11}$, $R_{12}$, $R_{13}$, $R_{14}$, $R_{15}$, $R_{16}$, $R_{17}$ are defined in Table 1 below.

Exemplary biotransformed taxanes of the present invention include, but are not limited to, those of the following Formula I where $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$ are defined in Table 1 below.

TABLE 1

| Compound | $R_1$[1] | $R_2$ | $R_3$ | $R_4$ | $R_5$ | $R_6$[3] | $R_7$[2] |
|---|---|---|---|---|---|---|---|
| 1) paclitaxel | tax | $CH_3$ | H | β-acetyloxy | =O | β-$CH_3$ | β-OH |
| 2) 10-deacetylcephalomannine | ceph | $CH_3$ | H | β-OH | =O | β-$CH_3$ | β-OH |
| 3) 7-epitaxol | tax | $CH_3$ | H | β-acetyloxy | =O | β-$CH_3$ | α-OH |
| 4) 10-deacetyl-7-epi-taxol | tax | $CH_3$ | H | β-OH | =O | β-$CH_3$ | α-OH |
| 5) 7-epicephalomannine | ceph | $CH_3$ | H | β-acetyloxy | =O | β-$CH_3$ | α-OH |
| 6) baccatin III | α-OH | $CH_3$ | H | β-acetyloxy | =O | β-$CH_3$ | β-OH |
| 7) 10-deacetyl baccatin III | α-OH | $CH_3$ | H | β-OH | =O | β-$CH_3$ | β-OH |
| 8) cephalomannine | ceph | $CH_3$ | H | β-acetyloxy | =O | β-$CH_3$ | β-OH |
| 9) 10-deacetyl taxol | tax | $CH_3$ | H | β-OH | =O | β-$CH_3$ | β-OH |
| 10) 7-xylosyl taxol | tax | $CH_3$ | H | β-acetyloxy | =O | β-$CH_3$ | β-xylosyl |
| 11) 7-xylosylcephalomannine | ceph | $CH_3$ | H | β-acetyloxy | =O | β-$CH_3$ | β-xylosyl |
| 12) taxagifine | =O | α-$CH_3$ | β-OH | β-acetyloxy | α-acetyloxy | β-$CH_3$ | β-acetyloxy |
| 13) δ-benzoyloxy-taxagifine | =O | α-$CH_3$ | β-OH | β-acetyloxy | α-acetyloxy | β-benzoyloxymethyl | β-acetyloxy |
| 14) 9-acetyloxy-taxusin | α-acetyloxy | $CH_3$ | H | β-acetyloxy | α-acetyloxy | β-$CH_3$ | H |
| 15) 9-hydroxy-taxusin | α-acetyloxy | $CH_3$ | H | β-acetyloxy | α-OH | β-$CH_3$ | H |
| 16) taxane la | tax | $CH_3$ | H | =O | =O | β-$CH_3$ | α-OH |
| 17) taxane lb | taxsub | $CH_3$ | H | =O | =O | β-$CH_3$ | α-OH |
| 18) taxane lc | taxsub | $CH_3$ | H | =O | =O | β-$CH_3$ | α-acetyloxy |
| 19) taxane ld | α-acetyloxy | $CH_3$ | H | β-acetyloxy | α-acetyloxy | β-$CH_3$ | β-acetyloxy |
| 20) 7-epibaccatin III | α-OH | $CH_3$ | H | β-acetyloxy | =O | β-$CH_3$ | α-OH |

| Compound | $R_8R_{17}$ | $R_9R_{10}$[4] | $R_{11}$ | $R_{12}$[6] | $R_{13}$ | $R_{14}$ | $R_{15}$[5] | $R_{16}$ |
|---|---|---|---|---|---|---|---|---|
| 1) paclitaxel | H | oxetane | α-acetyloxy | α-benzoyloxy | β-OH | H | $CH_3$ | $CH_3$ |
| 2) 10-deacetylcephalomannine | H | oxetane | α-acetyloxy | α-benzoyloxy | β-OH | H | $CH_3$ | $CH_3$ |
| 3) 7-epitaxol | H | oxetane | α-acetyloxy | α-benzoyloxy | β-OH | H | $CH_3$ | $CH_3$ |
| 4) 10-deacetyl-7-epi-taxol | H | oxetane | α-acetyloxy | α-benzoyloxy | β-OH | H | $CH_3$ | $CH_3$ |
| 5) 7-epicephalomannine | H | oxetane | α-acetyloxy | α-benzoyloxy | β-OH | H | $CH_3$ | $CH_3$ |
| 6) baccatin III | H | oxetane | α-acetyloxy | α-benzoyloxy | β-OH | H | $CH_3$ | $CH_3$ |
| 7) 10-deacetyl baccatin III | H | oxetane | α-acetyloxy | α-benzoyloxy | β-OH | H | $CH_3$ | $CH_3$ |
| 8) cephalomannine | H | oxetane | α-acetyloxy | α-benzoyloxy | β-OH | H | $CH_3$ | $CH_3$ |
| 9) 10-deacetyl taxol | H | oxetane | α-acetyloxy | α-benzoyloxy | β-OH | H | $CH_3$ | $CH_3$ |
| 10) 7-xylosyl taxol | H | oxetane | α-acetyloxy | α-benzoyloxy | β-OH | H | $CH_3$ | $CH_3$ |
| 11) 7-xylosylcephalomannine | H | oxetane | α-acetyloxy | α-benzoyloxy | β-OH | H | $CH_3$ | $CH_3$ |
| 12) taxagifine | H | α-cinnamoyloxy | methylene (=$CH_2$) | α-acetyloxy | β-H | H | cyclo | α-$CH_3$ |
| 13) δ-benzoyloxy-taxagifine | H | α-cinnamoyloxy | methylene (=$CH_2$) | α-acetyloxy | β-H | H | cyclo | α-$CH_3$ |
| 14) 9-acetyloxy-taxusin | H | α-acetyloxy | methylene (=$CH_2$) | H | H | H | $CH_3$ | $CH_3$ |
| 15) 9-hydroxy-taxusin | H | α-acetyloxy | methylene (=$CH_2$) | H | H | H | $CH_3$ | $CH_3$ |
| 16) taxane la | H | oxetane | α-acetyloxy | α-benzoyloxy | β-OH | H | $CH_3$ | $CH_3$ |
| 17) taxane lb | H | oxetane | α-acetyloxy | α-benzoyloxy | β-OH | H | $CH_3$ | $CH_3$ |
| 18) taxane lc | H | oxetane | α-acetyloxy | α-benzoyloxy | β-OH | H | $CH_3$ | $CH_3$ |
| 19) taxane ld | H | α-OH | epoxide | α-acetyloxy | β-OH | H | $CH_3$ | $CH_3$ |
| 20) 7-epibaccatin III | H | oxetane | α-acetyloxy | α-benzoyloxy | β-OH | H | $CH_3$ | $CH_3$ |

Footnotes
(1) "ceph" denotes

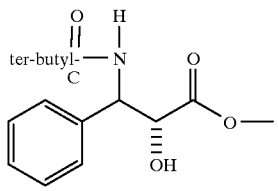

"tax" denotes

TABLE 1-continued

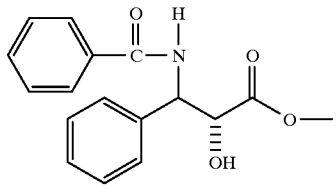

"taxsub" denotes

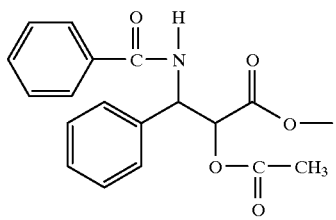

(2) "xylosyl" denotes

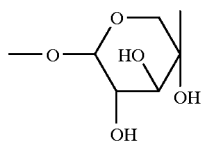

(3) "α" denotes the stereoposition of a stereomoiety below the plane of the taxane ring structure shown above

"β" denotes the stereoposition of a moiety above the plane of the taxane ring structure shown above

(4) "oxetane" denotes the moiety

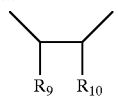

which is

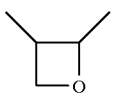

(5) "cyclo" denotes the cyclic group formed by bonding the group

to the taxane A ring as follows:

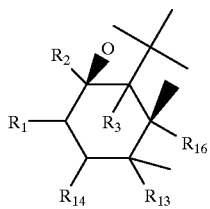

(6) "epoxide" denotes the moiety

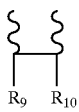

which is

The term "taxol-associated cytotoxic biological activity" is intended to mean a cytotoxic activity which is sufficient to promote the assembly of tubulin and stabilizes the resulting microtubules of cancer cells causing the division of the cells in two equal daughter cells to be interrupted; and sufficient to cause a disruption in the dynamic equilibrium which exists between microtubules and their depolymerized tubulin dimers, thus preventing completion of the mitotic step which causes a lethal metaphase arrest of cancer cells.

The expression "cancer cells" is intended to mean any cancer cells which include without limitation, ovarian, breast, lung, head and neck cancer cells.

The term "growth supporting nutrient medium" is intended to mean any culture media which include, without limitation, carbon sources, nitrogen sources, amino acids, vitamins and minerals.

The term "intercalating agent" is intended to mean any molecule binding to the double stranded DNA structure which include, without limitation, daunorubicine, ethidium bromide, acridine orange, acriflavine and epirubicine.

BRIEF DESCRIPTION OF THE DRAWINGS

FIG. 6 illustrates the cytotoxicity of organic extracts of microorganisms isolated from different species of Taxus on CRL-1572 cell line as well as the cytotoxicity of taxanes and paclitaxel negative bacteria (STJ.BRP.K1 and *E. coli* TG1);

Figure 7A:
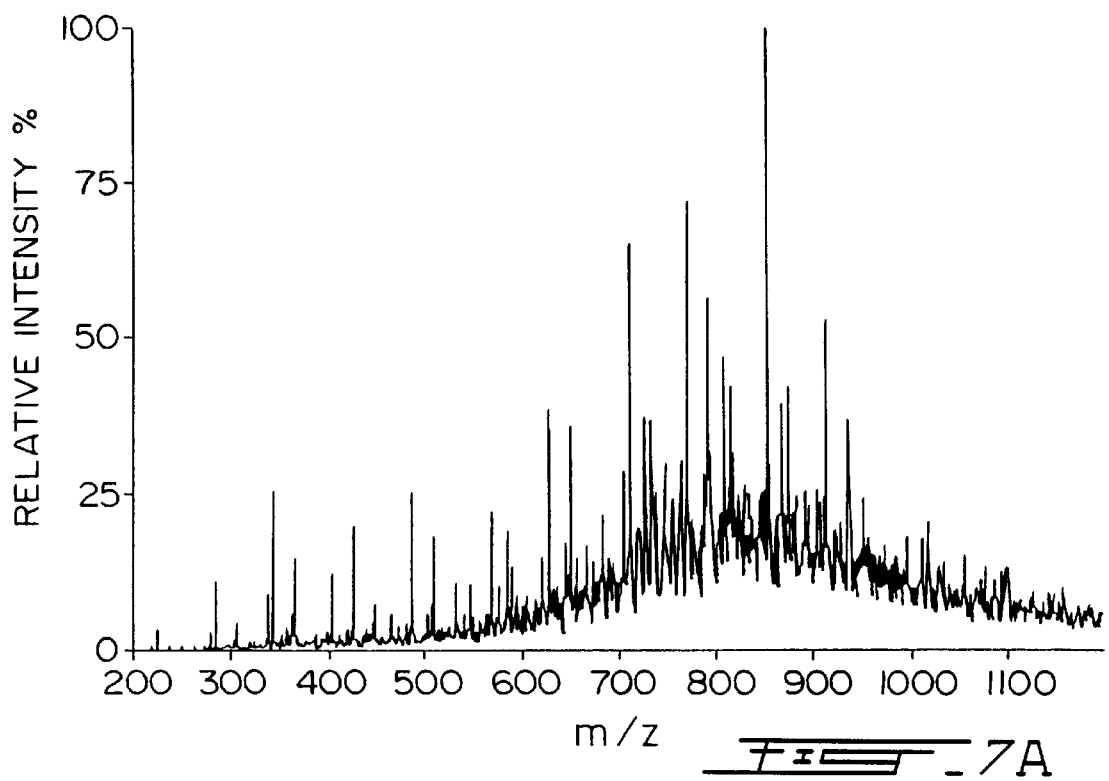

FIG. 7A illustrates the mass spectrometry of the substances eluted between 45 and 48 minutes using HPLC method no. 1 from an extract of *Sphingomonas taxi;*

Figure 7B:
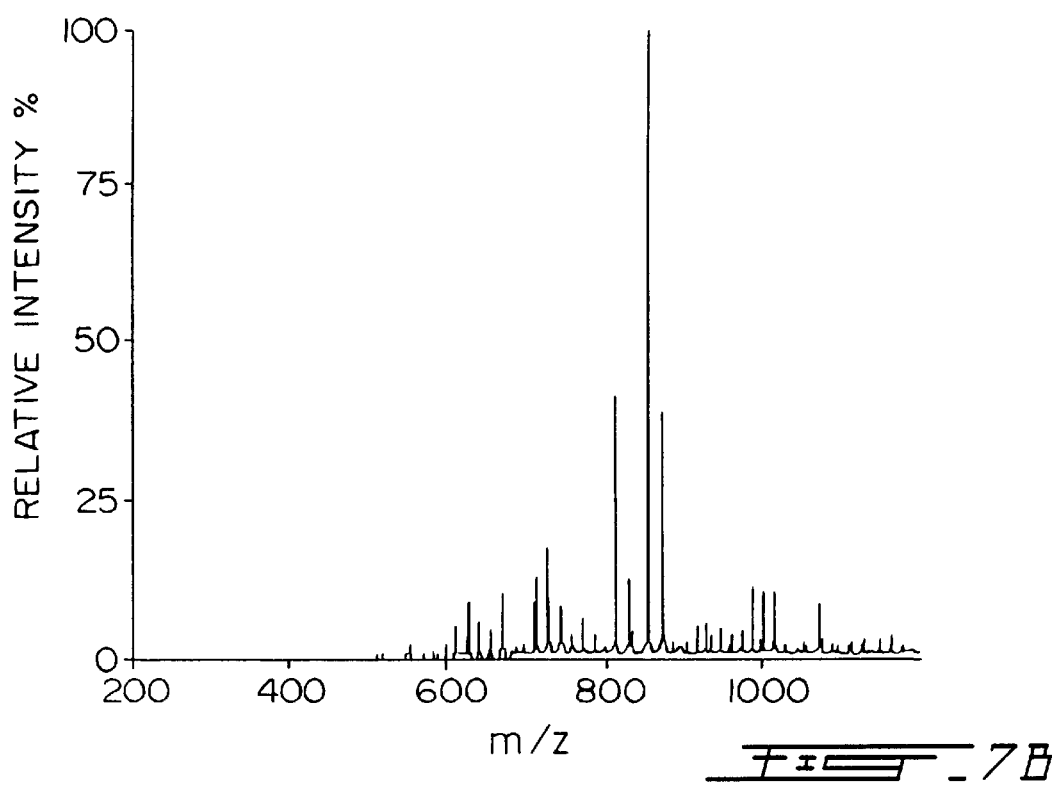
Figure 9A:
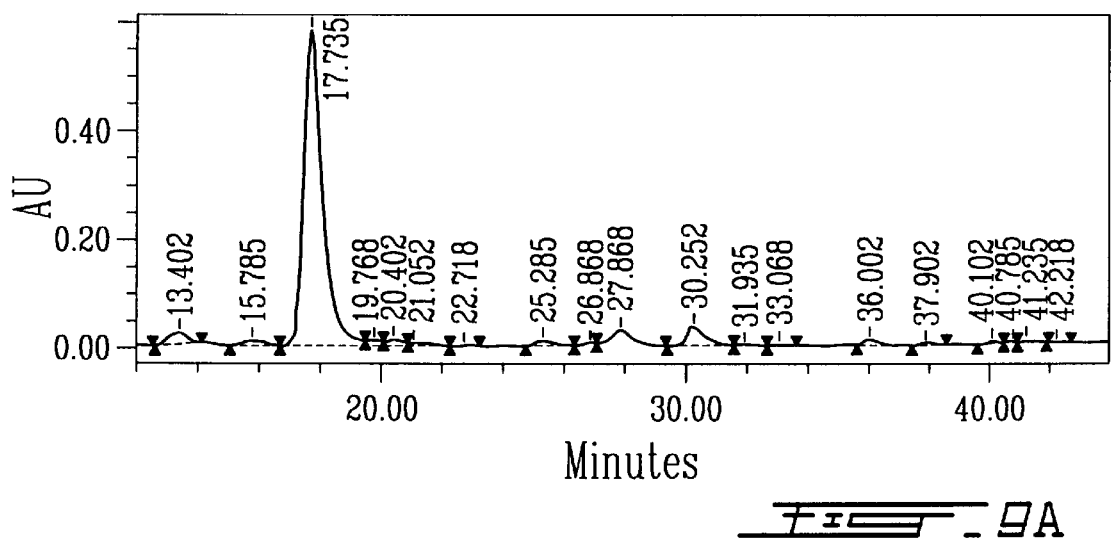
Figure 9B:
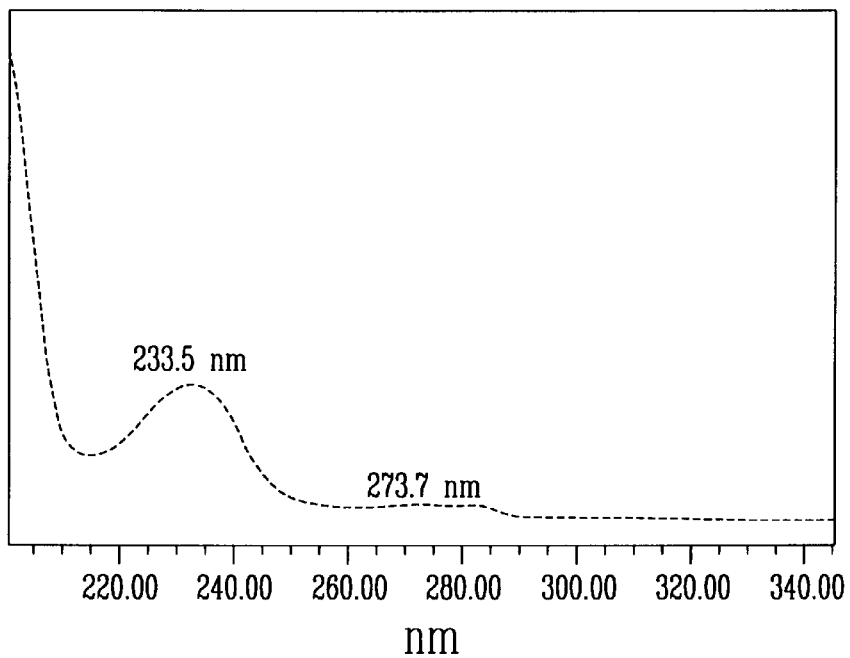

FIG. 7B illustrates the mass spectrometry of a paclitaxel standard;

FIG. 8A illustrates the almost complete 16S rRNA gene sequence of *Sphingomonas taxi* (SEQ ID NO:1);

FIG. 8B illustrates the almost complete 16S rRNA gene sequence of *Bacillus cereus* ssp. *taxi* (SEQ ID NO:2);

FIG. 8C illustrates the partial 16S rRNA gene sequence of *Bacillus megaterium* ssp. *taxi* (SEQ ID NO:3);

FIG. 8D illustrates the partial 16S rRNA gene sequence of Pantoea sp. BCM 1 (SEQ ID NO:4);

FIG. 8E illustrates the partial 16S rRNA gene sequence of *Bacillus cereus* ssp. BCM 4 (SEQ ID NO:5);

FIG. 8F illustrates the partial 16S rRNA gene sequence of a bacteria in accordance with one embodiment of the present invention, referred to as *Bacillus subtilis* ssp. *taxi* (SEQ ID NO:6);

FIG. 8G illustrates the partial 16S rRNA gene sequence of a bacteria in accordance with one embodiment of the present invention, referred to as Pantoea sp. BCM 2 (SEQ ID NO:7);

FIG. 8H illustrates the partial 16S rRNA gene sequence of a bacteria in accordance with one embodiment of the present invention, referred to as Pantoea sp. BCM 3 (SEQ ID NO:8);

FIG. 8I illustrates the partial 16S rRNA gene sequence of a bacteria in accordance with one embodiment of the present invention, referred to as *Bacillus megaterium* ssp. BCM 9 (SEQ ID NO:9);

FIG. 8J illustrates the partial 16S rRNA gene sequence of a bacteria in accordance with one embodiment of the present invention, referred to as Curtobacterium sp. BCM 5 (SEQ ID NO:10);

FIG. 8K illustrates the partial 16S rRNA gene sequence of a bacteria in accordance with one embodiment of the present invention, referred to as Sphingomonas sp. BCM 7 (SEQ ID NO:11);

FIG. 9A illustrates a typical chromatogram of an organic extract from the supernatant of *Bacillus cereus* ssp. *taxi* producing a specific bacterial taxane using HPLC method no. 2;

FIG. 9B illustrates the ultraviolet spectrum of the characteristic taxane produced by *Bacillus cereus* ssp. *taxi;*

Figures 10A, 10B:
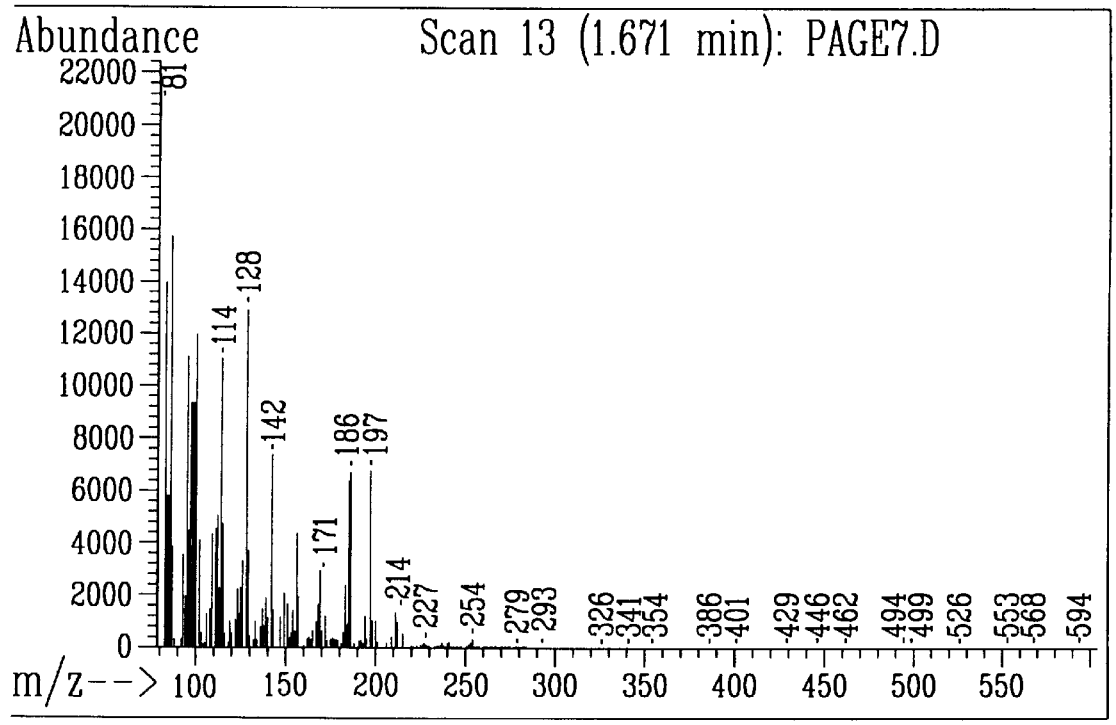
Figure 13:
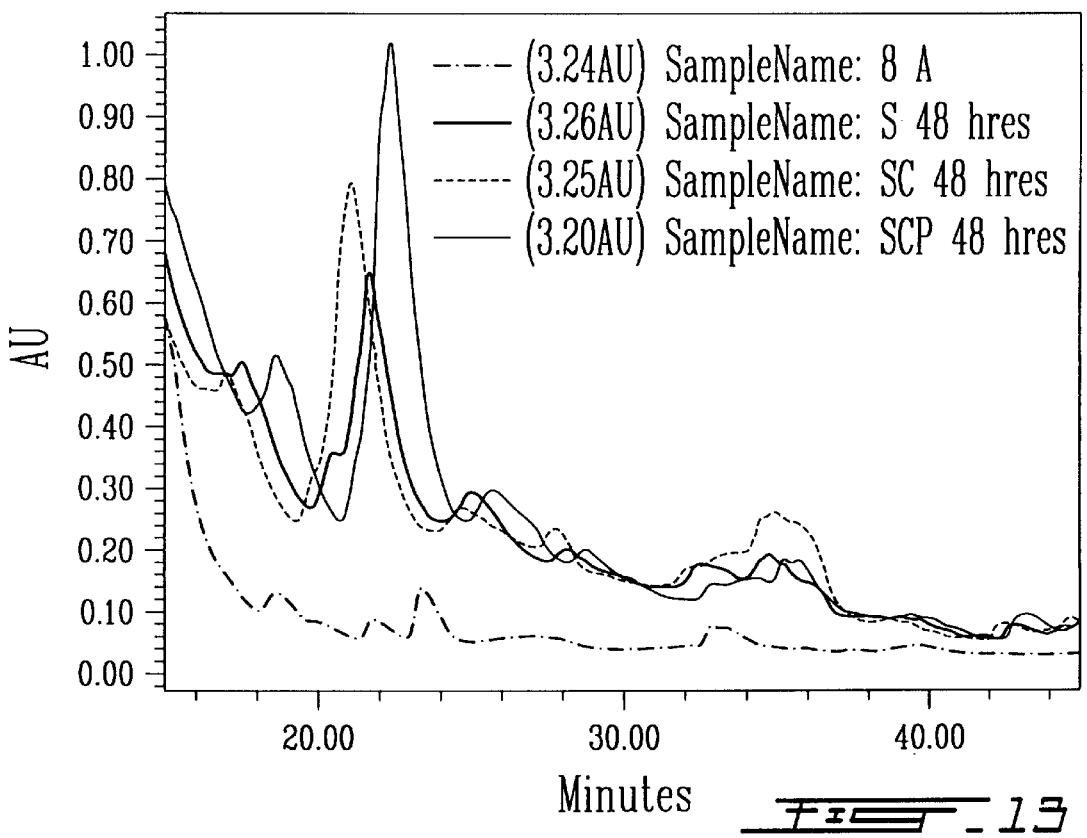
Figure 14C:
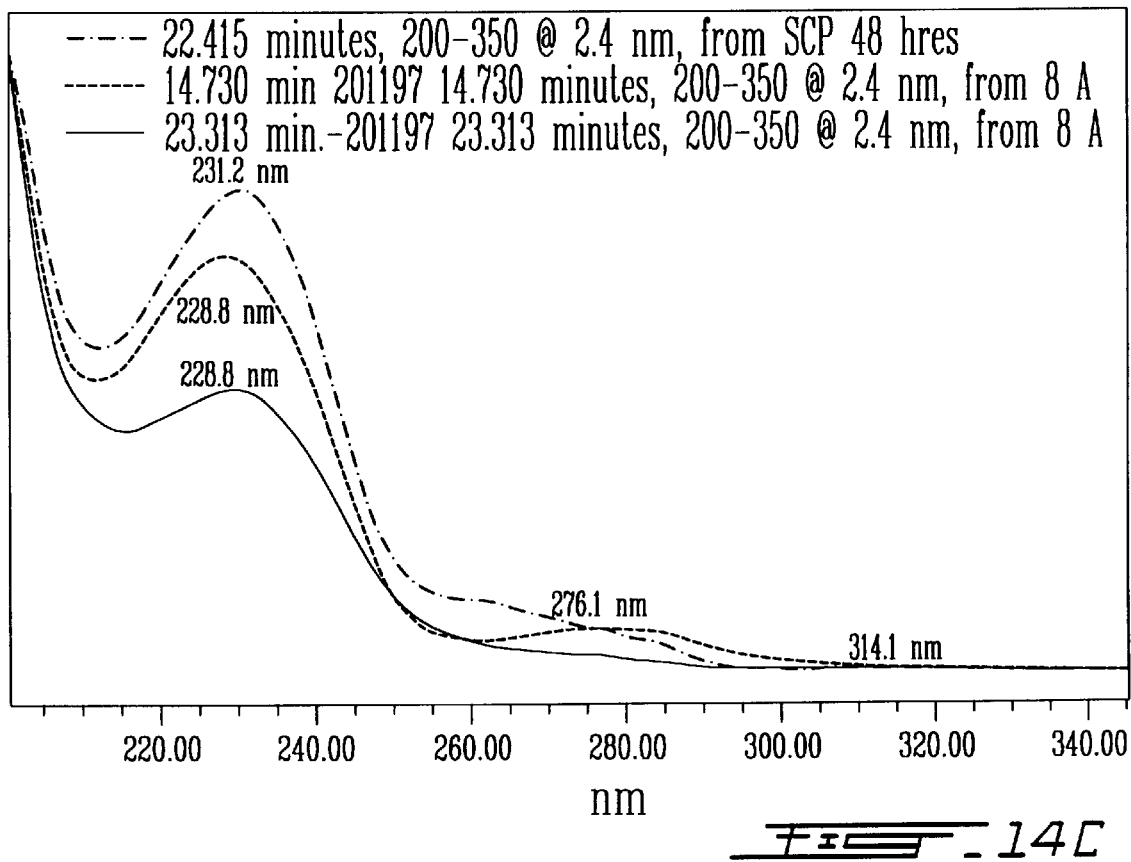

FIG. 10A illustrates the GC/MS (EI) spectrum of the purified specific bacterial taxane produced by *Bacillus cereus* ssp. *taxi* in accordance with the present invention;

FIG. 10B illustrates the mass-to-charge ratios of ions present in the EI mass spectra of the bacterial taxane produced by *Bacillus cereus* ssp. *taxi;*

FIG. 11A shows the evolution in time of two taxanes in the sterile culture medium supplemented with 1% v/v of an aqueous extract of Taxus canadensis incubated at 150 rpm at 30° C.;

FIG. 11B shows the evolution of two taxanes transformed by *Sphingomonas taxi* when cultured in the culture medium S-7 supplemented with 1% of an aqueous extract of Taxus canadensis, shaken at 150 rpm at 30° C.;

FIG. 12 shows the HPLC chromatograms of *S. taxi* cultured in the S-7 culture medium supplemented with 1% v/v of an aqueous extract of *Taxus canadensis* where sample name 8A represents the organic extract of the culture medium supplemented with 1% v/v of an aqueous extract of *Taxus canadensis,* sample name S 24 hres represents the organic extract of *Sphingomonas taxi* incubated 24 hours in the culture medium supplemented with 1% v/v of an aqueous extract of *Taxus canadensis*, sample name S 48 hres represents the organic extract of *Sphingomonas taxi* incubated 48 hours in the culture medium supplemented with 1% v/v of an aqueous extract of *Taxus canadensis*, and sample name S 72 hres represents the organic extract of *Sphingomonas taxi* incubated 72 hours in the culture medium supplemented with 1% v/v of an aqueous extract of *Taxus canadensis*;

FIG. 13 compares HPLC chromatograms of the supernatant extracts of *S. taxi* (sample name: S 48 hres), *S. taxi* D200 (sample name: SC 48 hres) and *S. Taxi* D201 (sample name: SCP 48 hres) cultured 48 hours in the medium S-7 supplemented with 1% v/v of an aqueous extract of *Taxus canadensis*, and the organic extract of the medium S-7 supplemented with 1% v/v of an aqueous extract of *Taxus canadensis* (sample name 8A); and FIGS. 14A–14C show the characteristic ultraviolet spectrum of the new biotransformed pro-taxanes.

DETAILED DESCRIPTION OF THE INVENTION

Plants are hosts of a variety of microorganisms. The relation between the plant and the microorganism can be saprophytic, parasitic, endophytic or symbiotic. Whatever the relation, there may be genetic exchange between the species. Taxus, such as *Taxus canadensis*, which grows in some regions of the province of Quebec, shows significant amounts of paclitaxel in its needles and stems. Samples of *Taxus canadensis* from seven (7) regions of the province of Quebec were chosen as well as samples of different species of Taxus such as *Taxus brevifolia, T. cuspidata, T. baccata, T. hunnewelliana*. Several different bacteria of different genus, such as Sphingomonas, Bacillus, Pantoea, and Curtobacterium were isolated from inner parts of samples from different species of Taxus, and all demonstrated taxanes and/or paclitaxel-producing properties.

Bacteria described above, produced taxanes and paclitaxel in fermentation procedures. Bacteria are cultured in a appropriate growth supporting nutrient medium containing ingredients known to those skilled in the art for the cultivation of microorganisms. Specific examples of appropriate such media are given below. Temperature of cultivation ranges from 10° C. to 35° C., and aerobic cultivation is generally preferred.

Taxanes and paclitaxel are generally excreted in the supernatant, up to 10% of those substances remain in the cell. Taxanes and paclitaxel thereof may be extracted by performing an organic extraction with an appropriate solvents such as methylene chloride or ethyl acetate.

In accordance with the present invention, various bacteria producing taxanes and paclitaxel were isolated from different species of Taxus.

One bacterium isolated from *Taxus canadensis* allows for the production of taxanes and paclitaxel at a yield of 1 µg/L, referred to as *Sphingomonas taxi*, has been already deposited at the American Type Culture Collection but was identified as *Erwinia taxi* (ATCC, 12301 Parklawn Drive, Rockville, Md. 20852 USA) on Apr. 25, 1995 under deposit number ATCC 55669. The deposit is also available as required by Foreign Patent laws in countries wherein counterpart applications are filed.

The other strains of the present invention have been deposited at the American Type Culture Collection (ATCC, 12301 Parklawn Drive, Rockville, Md. 20852 USA) on Dec. 18, 1997 under deposit accession numbers as set forth below.

The deposit are also available as required by Foreign Patent laws in countries wherein counterpart applications are filed.

| Strain | ATCC No. |
|---|---|
| *Bacillus cereus* ssp. *taxi* | 202061 |
| *Bacillus megaterium* ssp. *taxi* | 202062 |
| Curtobacterium sp. BCM5 | 202063 |
| Pantoea sp. BCM2 | 202064 |
| *Bacillus megaterium* BCM9 | 202065 |
| *Bacillus cereus* BCM4 | 202066 |
| *Sphingomonas taxi* D201 | 202067 |
| *Sphingomonas taxi* D200 | 202068 |
| Sphingomonas sp. BCM7 | 202069 |
| Pantoea sp. BCM3 | 202070 |
| Pantoea sp. BCM1 | 202071 |
| *Bacillus subtilis* ssp. *taxi* | 202072 |

In accordance with one embodiment of the present invention, the bacteria isolated from different species of Taxus allow for the production of taxanes and paclitaxel thereof at a yield of 1 to 25 µg/L.

In accordance with the present invention, the bacteria isolated from different species of Taxus may be employed for the biotransformation of pro-taxanes.

Isolation of the different microorganisms producing taxanes and paclitaxel

Each plant was divided into 5 parts; needles, twigs, stems, bark and roots. Each inner part of the plant was verified for the presence of taxanes and paclitaxel producing microorganisms.

The surface of every part of the plant was sterilized with 95% ethanol and then, cut into small pieces with a sterile blade. Pieces were homogenized in sterile water with a POLYTRON™ that had also been sterilized with ethanol 95%. The resulting mix was used to inoculate two different culture media; R2A agar (Difco) and Sabouraud agar (Difco).

Each plate was incubated at 22° C. and examined on a day-to-day basis. The morphology of each colony was meticulously noted and the bacteria were transferred on different media until a pure culture was obtained. A Gram coloration of every bacteria was done before the culture was frozen at −80° C.

Over 50 bacteria were isolated from different samples of *Taxus canadensis* of the province of Quebec. In addition, over 30 different bacteria were isolated from different species of Taxus which include, without limitations, *Taxus brevifolia, T. baccata, T. cuspidata, T. hunnewelliana*. Some of them, showing taxanes and paclitaxel production capacities, will be fully described below.

Screening of microorganisms

In order to verify the production of taxanes and paclitaxel by microorganisms, each organism was cultured in at least 500 ml of a growth supporting nutrient medium. Any liquid medium allowing taxanes and paclitaxel thereof production may be employed. Exemplary liquid media are S-7 media (Table 2), and defined media for Bacillus (Table 3). Every culture was performed in culture flasks and incubated at a temperature ranging from 20° C. to 35° C. with constant shaking until a sufficient growth was achieved, generally 18 to 72 hres.

TABLE 2

Composition of S-7 medium

| Compounds | g/L |
|---|---|
| glucose | 1 |
| fructose | 3 |
| sucrose | 6 |
| sodium acetate | 1 |
| soytone | 1 |
| thiamine | 0.001 |
| biotine | 0.001 |
| pyridoxal-HCl | 0.001 |
| Ca pantothenate | 0.001 |
| $MgSO_4$ | 0.0036 |
| $CaNO_3$ | 0.0065 |
| $Cu(NO_3)_2$ | 0.001 |
| $ZnSO_4$ | 0.0025 |
| $MnCl_2$ | 0.005 |
| $FeCl_3$ | 0.002 |
| phenylalanine | 0.005 |
| sodium benzoate | 0.1 |
| $KH_2PO_4$ 1M (pH 6.8) | 1 ml |

TABLE 3

Composition of the defined medium for Bacillus

| Compounds | g/L |
|---|---|
| L-glutamic acid | 10 |
| glucose | 5 |
| citric acid | 1 |
| $K_2HPO_4$ | 0.5 |
| $KH_2PO_4$ | 0.5 |
| $MgSO_4$—$7H_2O$ | 0.2 |
| $MnSO_4$—$4H_2O$ | 0.01 |
| $FeSO_4$—$7H_2O$ | 0.01 |

The culture was then centrifuged and the pellet separated from the supernatant by decantation. To verify if taxanes and paclitaxel were secreted in the medium or if it was confined within the cells, both were tested for the presence of the drug. Since taxanes and paclitaxel are hydrophobic, and in order to concentrate each sample, an extraction with an organic solvent was performed. For the pellet, the cells were dried and about 200 mg were powdered and ultrasonicated twice for 40 minutes in 3 ml methanol. The extracts were dried at 25° C. The residue was dissolved by adding 2 ml of methylene chloride and 2ml of distilled water. After appropriate shaking, the mixture was centrifuged at 4000 rpm for 5 min. The methylene chloride fraction was collected and dried under reduced pressure. Finally, the residue is dissolved in 0.5 ml of HPLC grade methanol.

The supernatant is extracted with one volume of methylene chloride. After appropriate shaking, the organic fraction is evaporated to dryness under reduced pressure. The residue is then resolubilized in 50 ml of methylene chloride and 50 ml of distilled water. After appropriate shaking, each fraction was collected and dried under reduced pressure. Each residue is dissolved in a measured minimal volume of HPLC grade methanol. All samples were kept frozen at −20° C.

a) HPLC screening

HPLC method no. 1

Some extracts were analyzed by High Performance Liquid Chromatography (HPLC) on a system consisting of a WATERS™ 625 LC pump, a WATERS™ 996 photodiode array spectrophotometer, and a WATERS™ 717plus autosampler. Chromatography was performed with a phenyl column from Waters (5im particle size, 6 mm×15 mm) with a guard module. The injection volume varies from 50 to 150 µl and the flow rate maintained at 1 ml/min. The following elution program was used;

0 to 20 min.: methanol:water:acetonitrile (20:65:15) ramped to methanol:water:aceto-nitrile (20:45:35)

20 to 50 min.: methanol:water:acetonitrile (20:45:35) ramped to methanol:water:acetonitrile (20:25:55)

50 to 60 min.: methanol:water:acetonitrile (20:25:55) ramped to methanol 100%

Figure 1A:
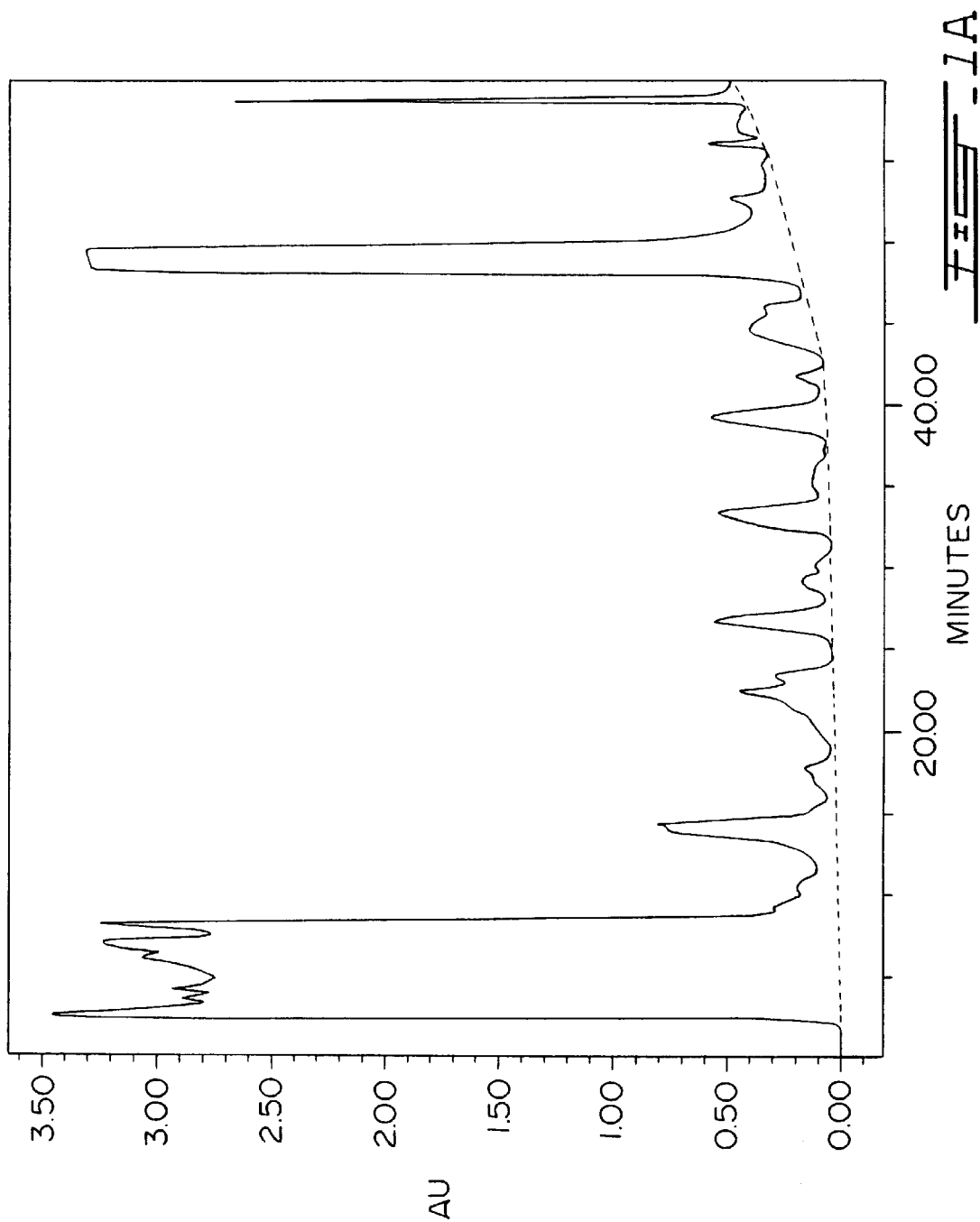
FIG. 1A shows the elution profile, according to HPLC method no. 1, of an organic supernatant extract of a bacteria in accordance with one embodiment of the present invention, referred to as *Sphingomonas taxi;*
Figure 1B:
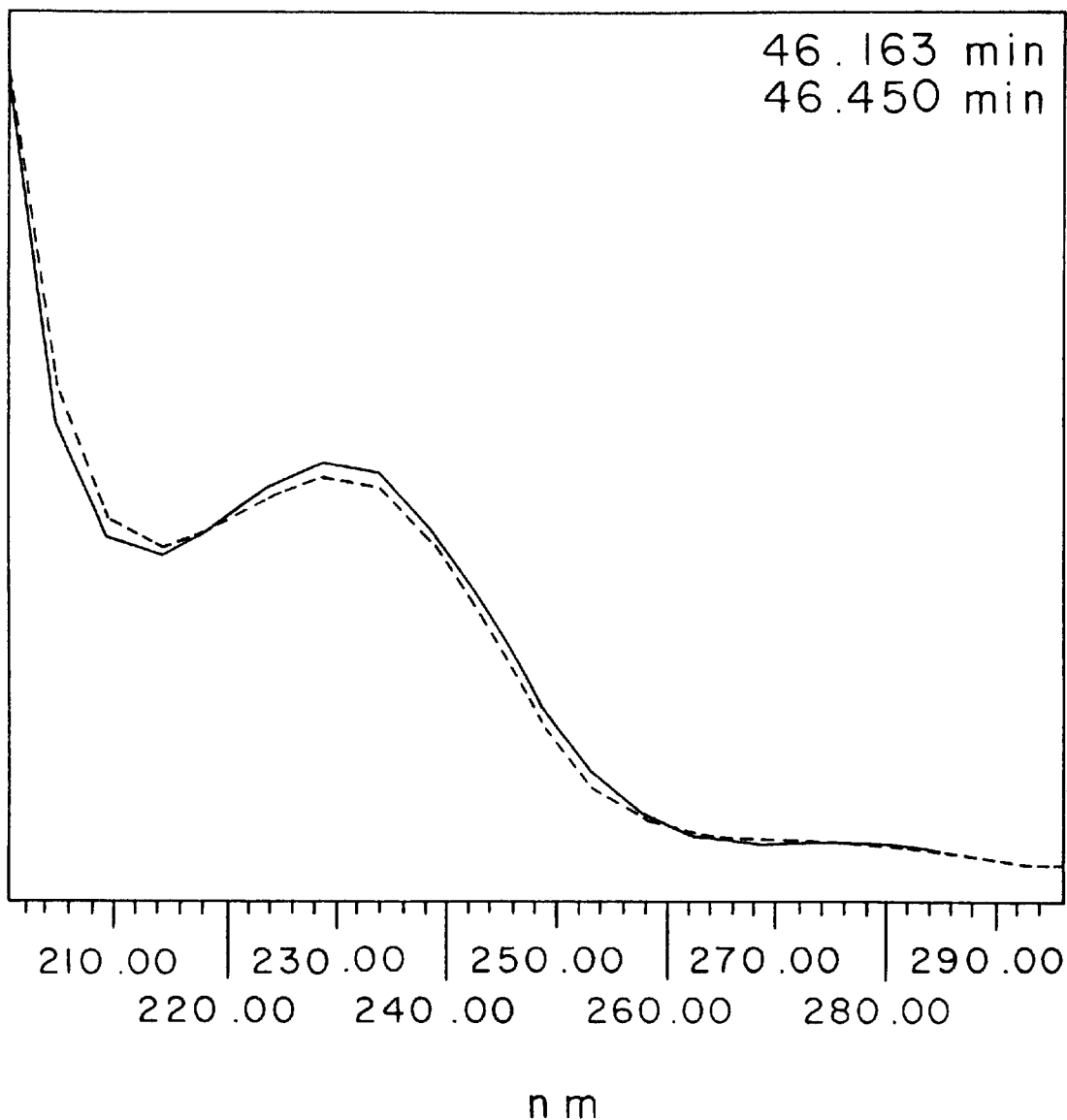
FIG. 1B illustrates the UV spectra of paclitaxel obtained from a standard and of an organic extract of supernatant of a bacteria in accordance with one embodiment of the present invention, referred to as *Sphingomonas taxi;*

Table 4 identifies the retention times of known authentic standards on HPLC methods no. 1 and no. 2. Using HPLC no. 1, paclitaxel has a retention time of 46 minutes. In FIG. 1, we show the ultraviolet spectrum of paclitaxel produced by *Sphingomonas taxi*. The spectrum is very characteristic with a second maximum of absorption at 230 nm. This figure illustrates that *Sphingomonas taxi* produces a compound having the same retention time and the same UV spectrum as paclitaxel.

HPLC method no. 2

Some extracts were analyzed on the same HPLC system with a curosil-PFP column (250 mm×3.2 mm) from Phenomenex with a guard module. Injections varied from 50 ul to 150 ul and the flow rate maintained at 0.8 ml/min. The following gradient program was used;

0 to 50 min.: acetonitrile:water (25:75) ramped to acetonitrile:water (65:35)

50 to 62.5 min.: acetonitrile:water (65:35) ramped to methanol 100%

62.5 to 65 min.: methanol 100% to acetonitrile:water (25:75)

65 to 75 min.: acetonitrile:water (25:75)

As shown in Table 4, using HPLC method no. 2, paclitaxel is eluted at 36.987 minutes.

TABLE 4

Retention time of taxanes standards using HPLC methods no. 1 and no. 2

| | Retention time using | |
|---|---|---|
| Taxanes | HPLC method no. 1 | HPLC method no. 2 |
| 10-deacetyl baccatin III | n/a | 12.037 min. |
| baccatin III | n/a | 20.670 min. |
| 7-xylosyl-10-deacetyltaxol B | n/a | 24.870 min. |
| 7-xylosyl-10-deacetyltaxol and taxinine M | n/a | 27.120 min. |
| 7-xylosyl-10-deacetyltaxol C | n/a | 28.770 min. |
| 10-deacetyltaxol and 7-xylosyltaxol | n/a | 30.770 min. |
| cephalomannine | n/a | 34.753 min. |
| 7-epi-10-deacetyltaxol | n/a | 35.703 min. |
| paclitaxel | 46 minutes | 36.987 min. |
| taxol C | n/a | 38.853 min. |
| 7-epitaxol | n/a | 42.287 min. |

Figure 2A:
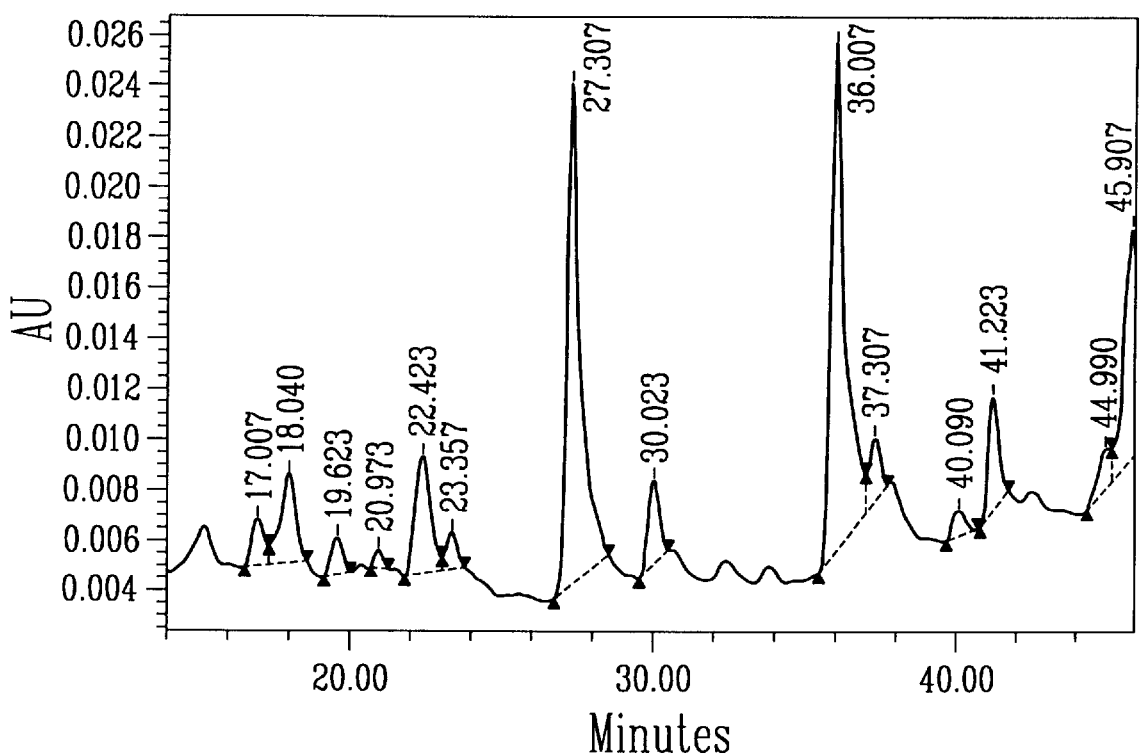
FIG. 2A illustrates a typical chromatogram of an organic extract of the supernatant of a bacteria in accordance with one embodiment of the present invention, referred to as *Bacillus cereus* ssp. *taxi* using HPLC method no. 2.
Figure 2B:
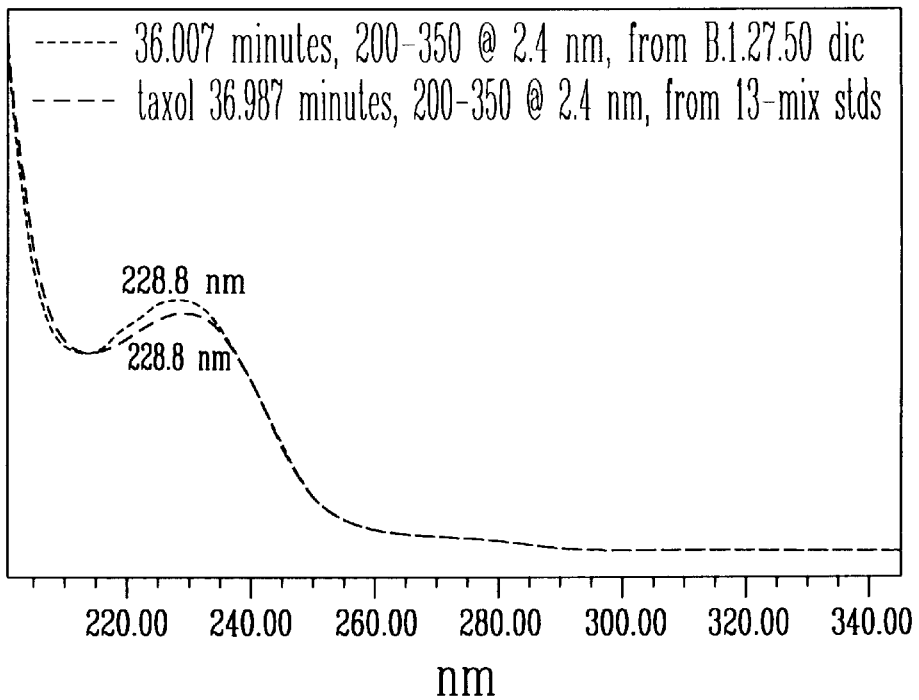
FIG. 2B illustrates the ultraviolet spectrum of paclitaxel produced by *Bacillus cereus* ssp. *taxi* compared to a paclitaxel standard.
Figure 2C:
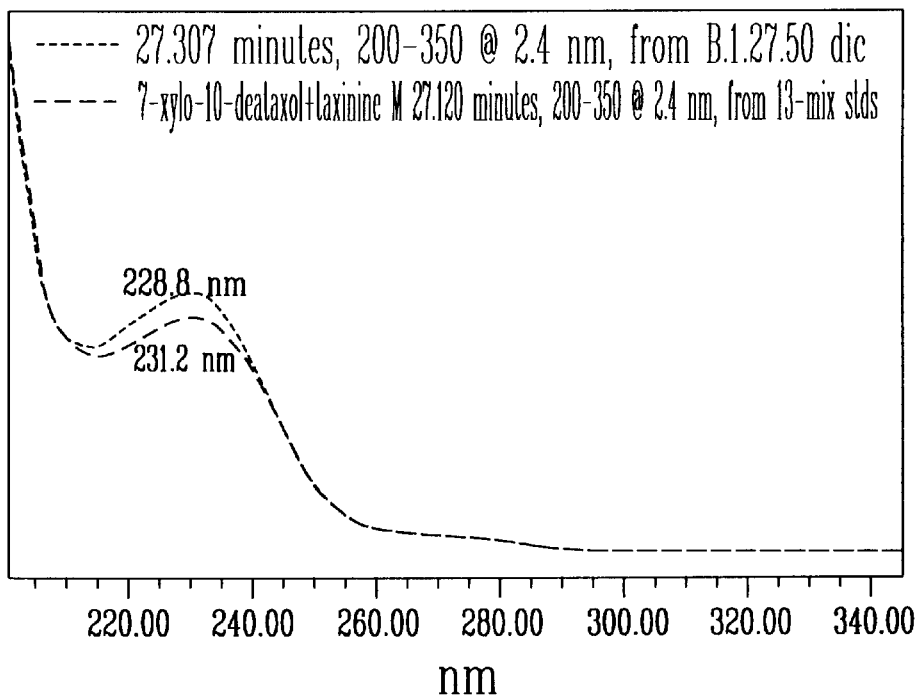
FIG. 2C illustrates the ultraviolet spectrum of 7-xylosyl-10-deacetyltaxol produced by *Bacillus cereus* ssp. *taxi* compared to an authentic standard co-eluting with taxinine M.

FIG. 2A shows a typical chromatogram of an organic extract of *Bacillus cereus* ssp. *taxi*, and in FIGS. 2B and 2C there is compared the UV spectra of the substances produced by Bacillus with authentic commercial plant standards. This figure clearly illustrates the ability of *Bacillus cereus* ssp. *taxi* to produce paclitaxel and 7-xylosyl-10-deacetyltaxol.

Figure 3A:
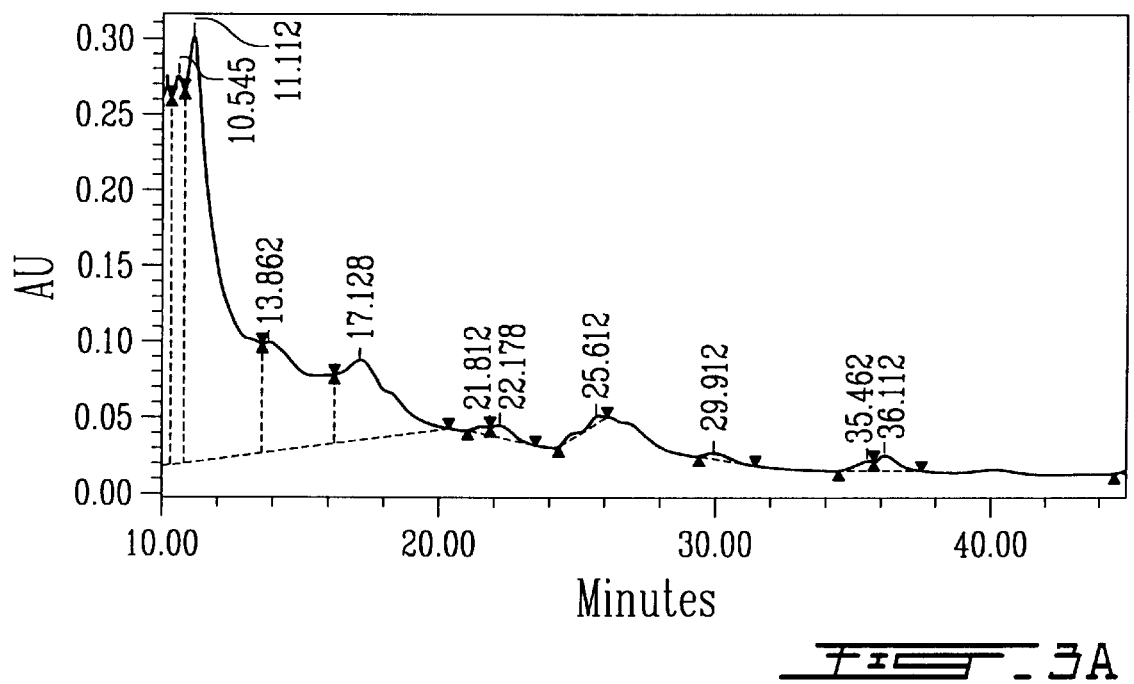
FIG. 3A illustrates a typical chromatogram of an organic extract of the supernatant of a bacteria in accordance with one embodiment of the present invention, referred to as Pantoea sp. BCM 1 using HPLC method no. 2.
Figure 3B:
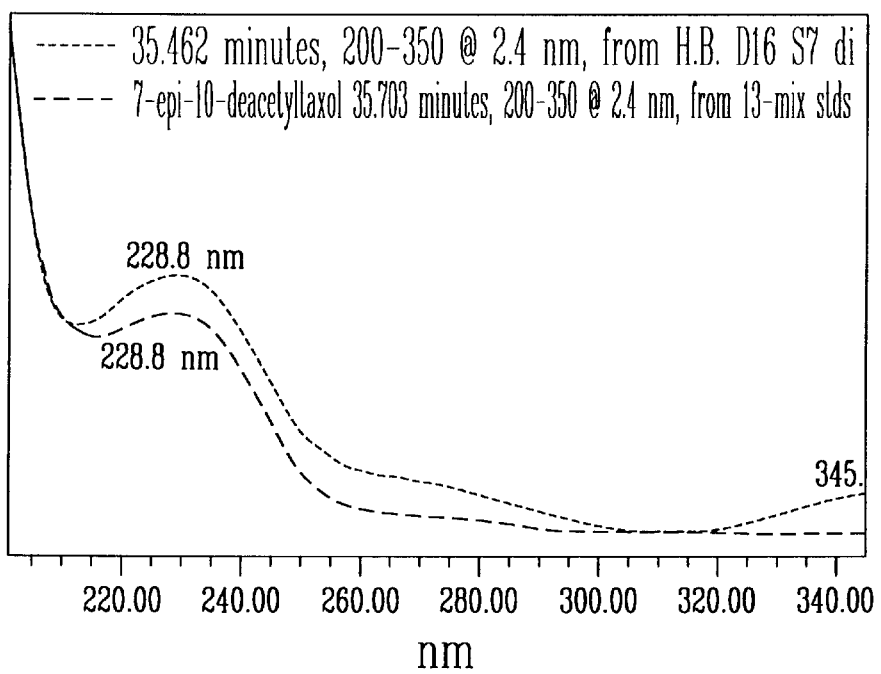
FIG. 3B illustrates the ultraviolet spectrum of 7-epi-10-deacetyltaxol produced by Pantoea sp. BCM 1 compared to an authentic standard.

FIG. 3A shows the typical HPLC chromatogram of the supernatant of Pantoea sp. BCM 1 and, in FIG. 3B there is compared the bacterial 7-epi-10-deacetyltaxol against an authentic commercial plant standard, establishing the production of 7-epi-10-deacetyltaxol by Pantoea sp. BCM 1.

Figure 4A:
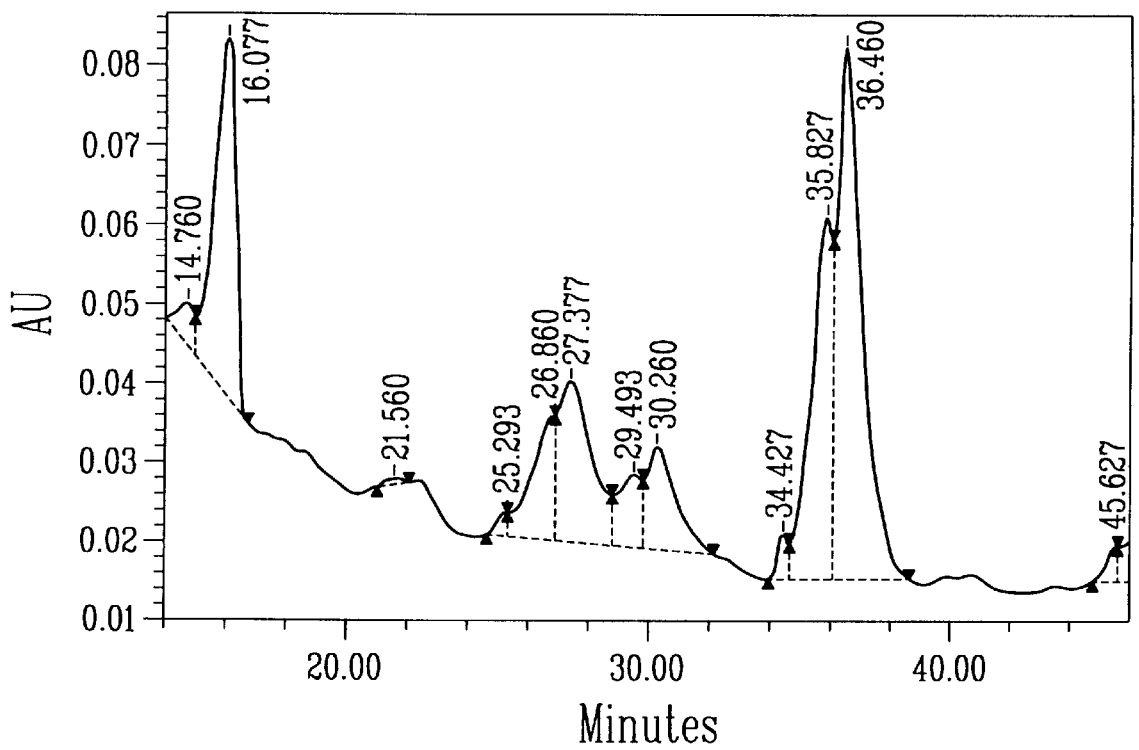
FIG. 4A illustrates a typical chromatogram of an organic extract of the supernatant of a bacteria in accordance with one embodiment of the present invention, referred to as *Bacillus megaterium* ssp. *taxi* using HPLC method no. 2.
Figure 4B:
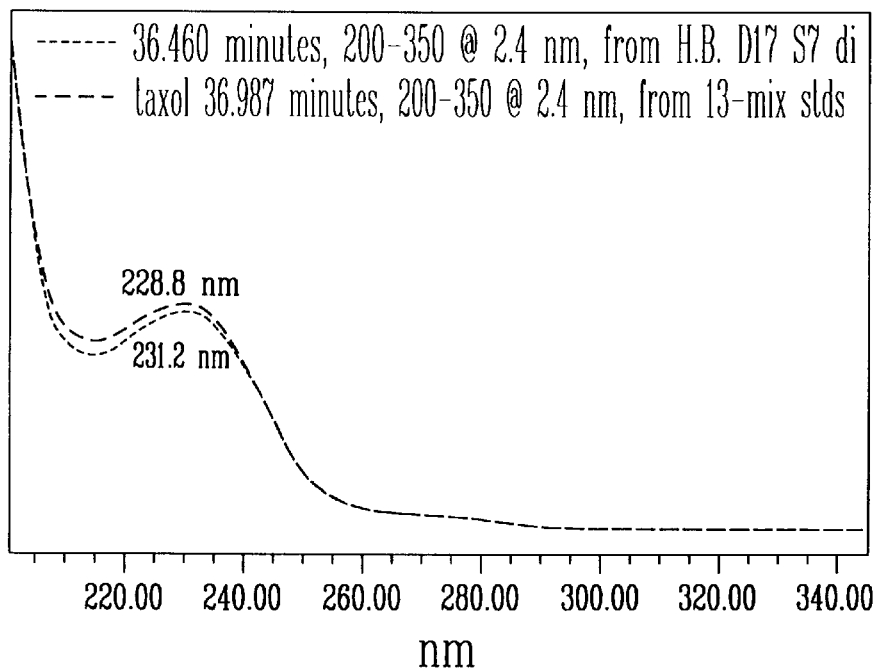
FIG. 4B illustrates the ultraviolet spectrum of the bacterial paclitaxel produced by *Bacillus megaterium* ssp. *taxi* compared to an authentic standard.

FIG. 4A shows a typical chromatogram of *Bacillus megaterium* ssp. *taxi* and, in FIG. 4B there is compared the ultraviolet spectrum of the bacterial paclitaxel with an authentic standard proving the capacity of this bacterium to produce paclitaxel.

Figure 5A:
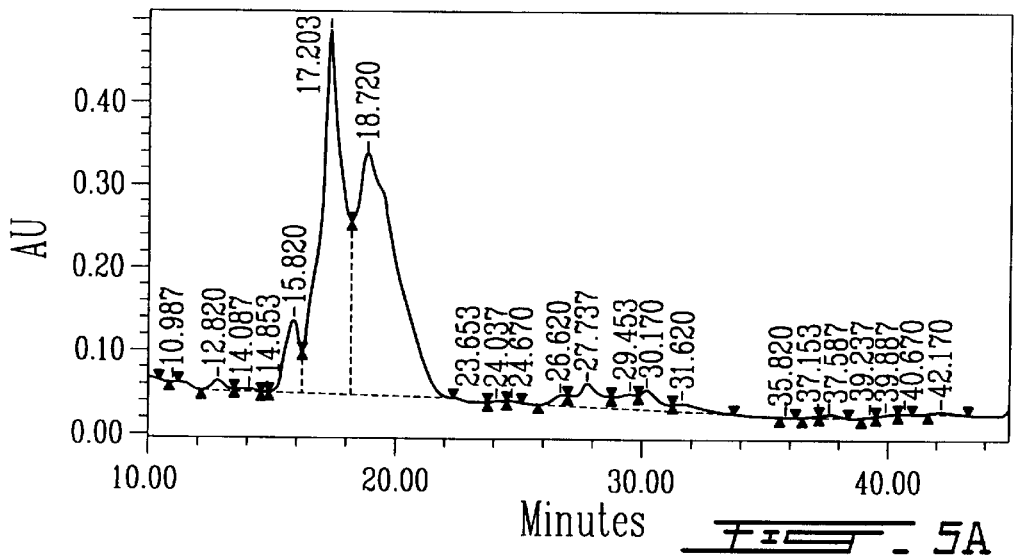
FIG. 5A illustrates a typical chromatogram of an organic extract of the supernatant of a bacteria in accordance with one embodiment of the present invention, referred to as *Bacillus cereus* ssp. BCM 4 using HPLC method no. 2.
Figure 5B:
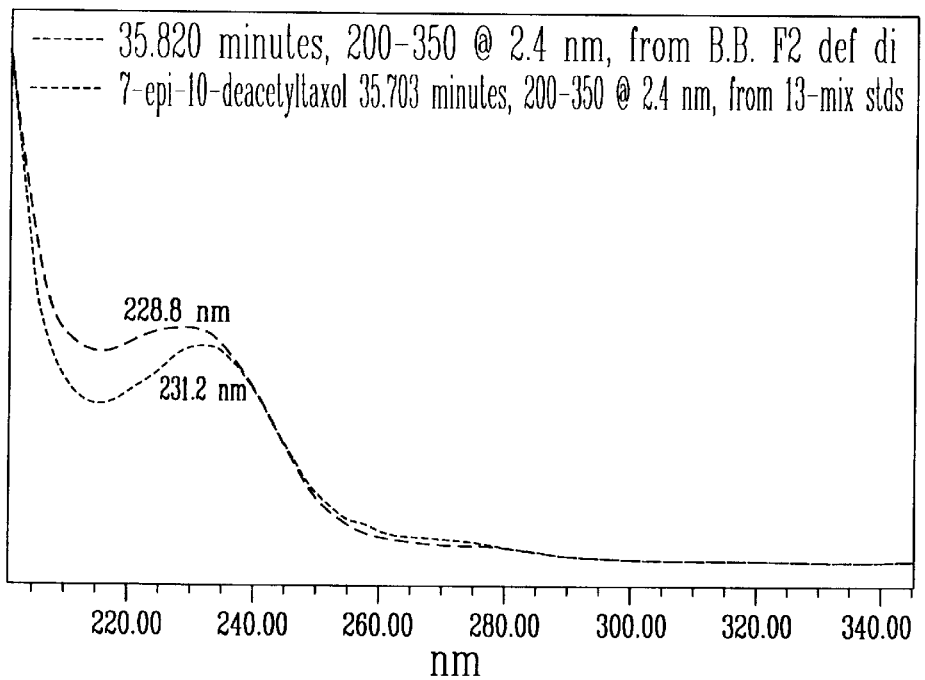
FIG. 5B shows a substance having the characteristic ultraviolet spectrum of a taxane compared to a standard of 7-xylosyl-10-deacetyltaxol co-eluting with taxinine M.

FIG. 5A shows a typical chromatogram of *Bacillus cereus* ssp. BCM 4 and, FIG. 5B shows a substance having the characteristic ultraviolet spectrum of a taxane compared to a standard of 7-xylosyl-10-deacetyl-taxol co-eluting with taxinine M, proving the capacity of *Bacillus cereus* ssp. BCM 4 to produce taxanes.

b) Cytotoxicity on cancer cells

An ovarian cancer cell line obtained from American Type Culture Collection (12301 Parklawn Drive, Rockville, Md. 20852 USA) under ATCC accession number CRL-1572) was chosen for the investigation. Briefly, 2000 cells/well of a 96-well microplate were inoculated. After 2 days, different dilutions of the drug were added in a volume of 100 $\mu$l. Three days later, the viability of cells was measured with ALAMAR™ blue (B. Pagé et al. 1993, *Intl. J. of Oncology,* 3:473–476). The ATCC CRL-1572 cell line is particularly sensitive to paclitaxel ($ID_{50}$ of 1 ng/ml). Microbial extracts have also been tested for their cytotoxicity on those cells. FIG. 6 shows the cytotoxicity of different bacterial supernatant extracts. This figure clearly demonstrates that culture supernatant extracts from *Sphingomonas taxi* and *Bacillus cereus* ssp. *taxi* are at least 5-fold more cytotoxic than extracts from non-paclitaxel producing bacteria such as STJ.BRP.K1 and *E. coli* TG1.

c) Mass spectrometry

Mass spectrometry of the substances eluted between 45 and 48 minutes with HPLC method no.1 from an extract of *Sphingomonas taxi* was performed. FIG. 7A shows the results obtained. In every sample, a substance with a molecular weight (M.W.) of 853.5 daltons appears. The theoretical M.W. of paclitaxel is 854 daltons. Even if these extracts were partially purified, essentially the major compound obtained is paclitaxel.

d) Characterization of a bacterial taxane by EI/MS

FIG. 9A, shows a typical chromatogram of *Bacillus cereus* ssp. *taxi* producing a characteristic taxane having a retention time o f 15 minutes using HPLC method no. 2. In FIG. 9B, the characteristic ultraviolet spectrum of this substance is illustrated. It was purified on HPLC using HPLC method no. 2 and, analyzed in Electro Ionization Mass Spectrometry (EI/MS) as described by Thomas D. McClure et al. (*J. Am. Soc. Mass Spectrom.,* 1992, 3, pp. 672–679).

FIG. 10A shows the EI spectrum of this taxane and FIG. 10B shows the characteristic fragments of this taxane. Since this taxane has never been observed in plant extracts of different species of Taxus, and this compound is produced by at least two species of *Bacillus* (*cereus* ssp. *taxi* and *megaterium* ssp. *taxi*), we consider this novel taxane unique to microorganisms isolated from Taxus.

Characterization of taxane and paclitaxel producing microorganisms a) Biochemical and physiological characteristics Table 5 shows the species of Taxus from which each bacterium was isolated, the Gram coloration, the morphology of colonies on different culture media and, some biochemical characteristics. This Table clearly illustrates the diversity of our taxanes and-paclitaxel producing bacteria i.e. we have isolated and identified Gram-negative and Gram-positive rods including Actinomycetes from different species of Taxus which all possess taxanes and/or paclitaxel producing capacities.

TABLE 5

Cellular, morphological and biochemical characteristics of some taxanes and paclitaxel producing bacteria

| Name | Isolated from | Gram | Cellular morphology | Description of colonies on blood agar | Description of colonies on TA-1 | Catalase | Urease |
|---|---|---|---|---|---|---|---|
| *Sphingomonas taxi* | *Taxus canadensis* | – | Rod | No growth | 3 days to grow Orange-Opaque Glossy-Convexe Circular contour | + | – |
| *Bacillus cereus* ssp. *taxi* | *Taxus canadensis* | + | Rod | Double hemolysis Gray-green-Opaque Dry-Dull-Flat Irregular edge | Cream- Opaque Dry-Dull-Flat Irregular edge | + | – |
| *Bacillus megaterium* ssp. *taxi* | *Taxus hunnewelliana* | + | Rod | Gray- Opaque Dry-Dull Convex Irregular edge | Cream- Opaque Glossy Slightly convex Irregular edge | + | – |
| Pantoea sp. BCM 1 | *Taxus hunnewelliana* | – | Rod | Semi-translucent Glossy-Flat Regular edge | Cream with yellow pigment in middle Opaque-Glossy-Flat Regular edge | + | – |
| Pantoea sp. BCM 2 | *Taxus cuspidata* | – | Rod | Yellow Opaque Glossy-Flat Regular edge | Yellow Semi-translucent Glossy-Flat Regular edge | + | – |
| Pentoea sp. BCM 3 | *Taxus cuspidata* | – | Rod | Semi-translucent Glossy-Flat Regular edge | Yellow Semi-translucent Glossy-Flat Regular edge | + | – |
| *Bacillus cereus* ssp. BCM 4 | *Taxus brevifolia* | + | Rod | Double hemolysis Gray-green-Opaque Dry-Dull-Flat Irregular edge | Cream- Opaque Dry-Dull-Flat Irregular edge | + | – |
| *Bacillus subtilis* | *Taxus* | + | Rod | Semi-translucent | Cream- | + | – |

TABLE 5-continued

Cellular, morphological and biochemical characteristics of
some taxanes and paclitaxel producing bacteria

| Name | Isolated from | Gram | Cellular morphology | Description of colonies on blood agar | Description of colonies on TA-1 | Catalase | Urease |
|---|---|---|---|---|---|---|---|
| ssp. *taxi* | *baccata* | | | Dry, Dull Convex Regular edge | Translucent Dry, Dull Convex Regular edge | | |
| *Bacillus megaterium* ssp. BCM 9 | *Taxus hunnewelliana* | + | Rod | Gray- Opaque Dry-Dull Convex Irregular edge | Cream- Opaque Glossy Slightly convex Irregular edge | + | − |
| *Curtobacterium* sp. BCM 5 | *Taxus brevifolia* | + | Rod | 2 days to grow Cream Semi-translucent Glossy-Flat Regular edge | 2 days to grow Yellow Semi-translucent Glossy-Flat Regular edge | + | − |
| *Sphingomonas* sp. BCM 7 | *Taxus hunnewelliana* | − | Rod | No growth | 3 days to grow Orange-Opaque Glossy-Convex Regular edge | + | − | b) Identification of the genus of taxanes and paclitaxel producing microorganisms The genus of each taxanes and paclitaxel producing bacteria was determined by sequencing the 16S rRNA genes. Genomic DNA of each strain was used as template for PCR (Polymerase Chain Reaction). Primers based on conserved regions at the beginning and the end of the 16S rRNA gene, SSU-27 (5'-AGAGTTTGATCMTGGCTCAG-3'; SEQ ID NO:12), and SSU-1 492 (5'-TACGGYTACCTTGTTACGACTT-3'; SEQ ID NO:13), were used to amplify a portion of the 16S gene. The amplicons were purified with the "PCR purification kit" (sold by Qiagen) and sequenced using the ABI Prism System. Sequence analysis was performed using GCG software package (Genetics Computer Group Inc., Madison, Wis.).

FIG. 8A shows the almost complete sequence of the 16S rRNA gene of *Sphingomonas taxi*. Since this strain has unique biosynthetic capacities and more than 3% sequence difference with the 16S rRNA genes of other known species of Sphingomonas, we created a new species and named it *taxi* on the behalf of its isolation source. FIG. 8B shows the almost complete sequence of the 16S rRNA gene of *Bacillus cereus* ssp. *taxi*. Since this bacterium possesses unique metabolic capacities, and in order to differentiate this species from other known *Bacillus cereus*, we identified it by subspecies name *taxi* also on the behalf of its isolation source. In FIGS. 8C to 8L, we show partial sequences of the 16S rRNA genes of other taxanes and/or paclitaxel producing microorganisms.

Consequently, in accordance with the present invention, a plurality of bacteria isolated from different species of Taxus can be used for the mass production of paclitaxel and other taxanes. Based on the analysis of partial 16S rRNA gene sequences, and morphological and biochemical characteristics, we assigned the following genera, species, and subspecies or strain names to our paclitaxel and taxanes producing bacterial isolates; *Sphingomonas taxi, Bacillus cereus* ssp. *taxi, Bacillus megaterium* ssp. *taxi,* Pantoea sp. BCM 1, Pantoea sp. BCM 2, Pantoea sp. BCM 3, *Bacillus cereus* ssp. BCM 4, *Bacillus subtilis* ssp. *taxi, Bacillus megaterium* ssp. BCM 9, Curtobacterium sp. BCM 5 and Sphingomonas sp. BCM 7.

Biotransformation of taxanes a) Preparation of an aqueous extract of *Taxus canadensis*

Fresh cuttings of needles and small twigs (10 g) of a sample of *Taxus canadensis* are homogenized in 100 ml of distilled water. The solution is then centrifuged at 7000 rpm and the clear supernatant sterilized by filtration on a 0.22 μm filter. The solution is kept frozen at −20° C. until utilization.

b) Biotransformation of taxanes by taxanes and paclitaxel producing bacteria

The growth supporting nutrient medium S-7 is supplemented with 1% v/v on an aqueous extract of *Taxus canadensis*. This resulting supplemented medium is then inoculated with a thawed vial of a pure culture of one of our strain and incubated at 30° C. with constant shaking for a time sufficient to allow biotransformation of pro-taxanes.

The culture is then centrifuged and the remaining supernatant extracted with one volume of methylene chloride or ethyl acetate. After appropriate shaking, the organic fraction is evaporated to dryness under reduced pressure. The residue is then resolubilized in 50 ml of methylene chloride or ethyl acetate, and 50 ml of distilled water. After appropriate shaking, each fraction was collected and dried under reduced pressure. Each residues is dissolved in a measured minimal volume of HPLC grade methanol. All samples were kept frozen at −20° C. until analysis.

Figure 11A:
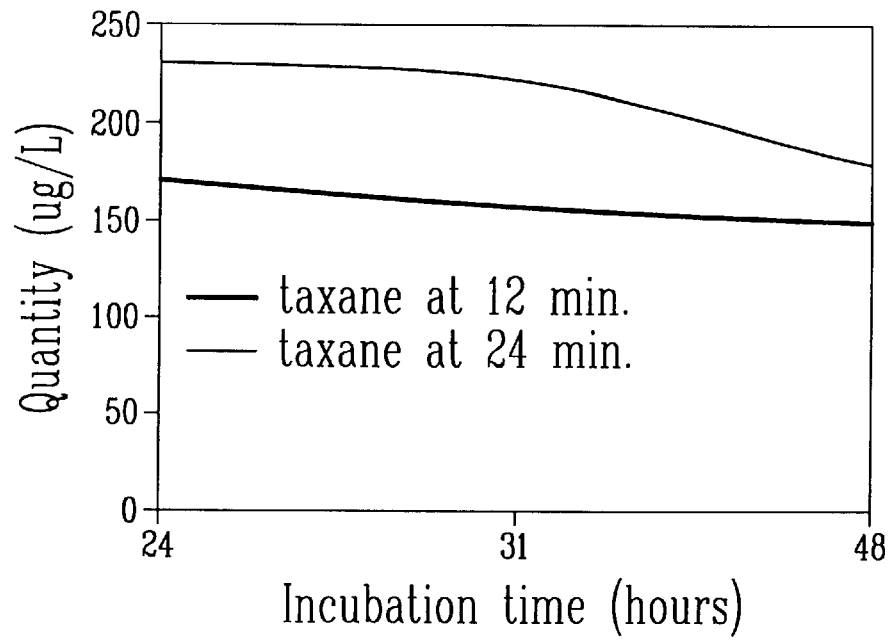
Figure 11B:
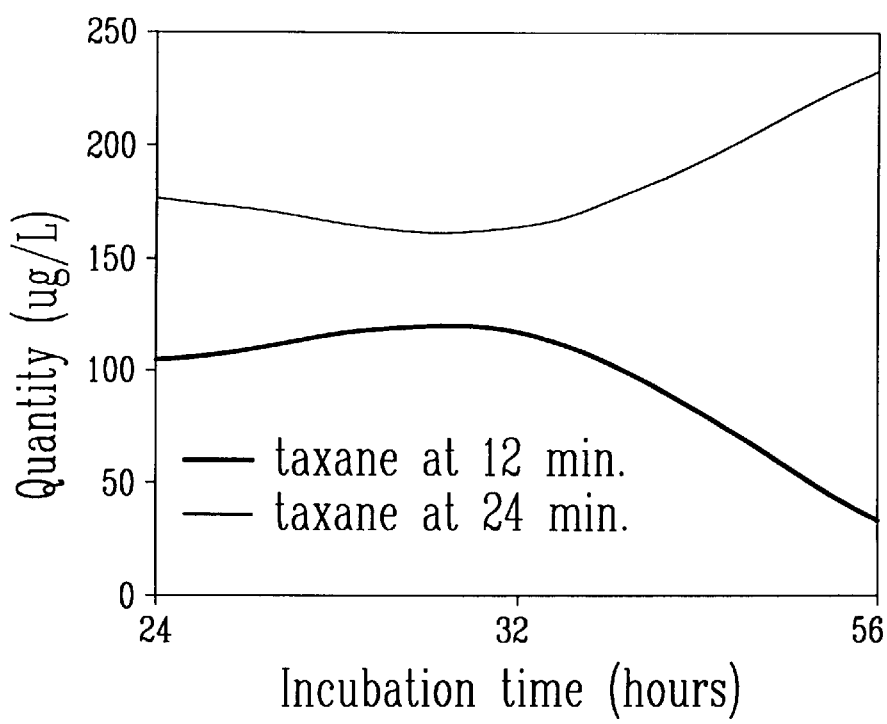

Samples were analyzed on HPLC using method no. 2. FIG. 11 shows the evolution of two taxanes in A) the sterile culture medium S-7 supplemented with 1% v/v of an aqueous extract of *Taxus canadensis* shaken at 150 rpm and incubated at 30° C., and in B) the supernatant of *Sphingomonas taxi* cultured in the culture medium S-7 supplemented with 1% v/v of an aqueous extract of *Taxus canadensis* shaken at 150 rpm and incubated at 30° C. This figure clearly illustrates that in the supernatant of *Sphingomonas taxi*, the diminution of the taxane eluted at 12 minutes corresponds to the proportional elevation of the taxane eluted at 24 minutes, proving the capacity of *Spingomonas taxi* to biotransform taxanes.

Figure 12:
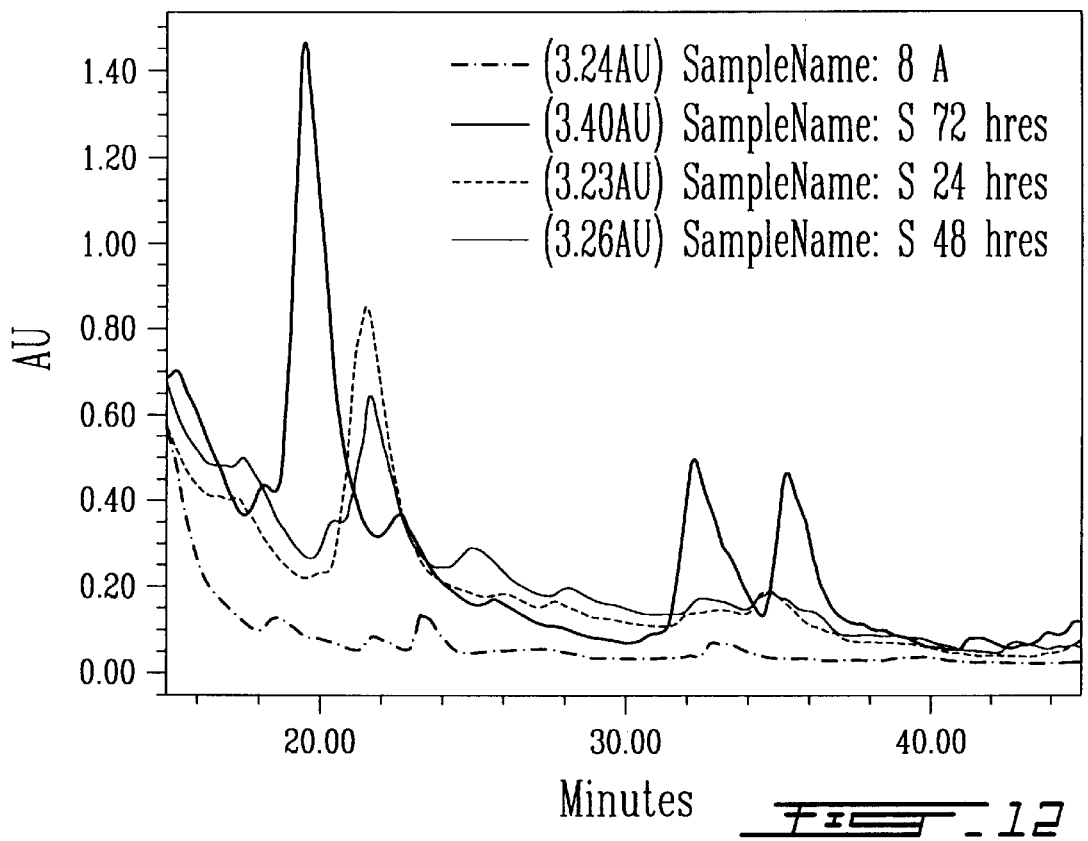

In addition, FIG. 12 compares the HPLC chromatogram of the organic extract of the culture supernatant of *S. taxi* incubated 24, 48 and 72 hours in the culture medium S-7 supplemented with 1% v/v of an aqueous extract of Taxus canadensis. This FIG. 12 clearly illustrates the production of pro-taxanes. The ultaviolet spectrum of one of these pro-taxanes is illustrated in FIG. 14A. FIG. 14A compares the UV spectrum of the new biotransformed taxane produced by *S. taxi* with taxanes from the aqueous extract of *Taxus canadensis*.

I. Mutagenesis of taxanes and paclitaxel producing bacteria

Typically, 20 ml of the culture medium TA-1 with 200 µg/ml of daunorubicin (purchased from Rhône-Poulenc) were inoculated with 500 µl of an overnight culture. The resulting broth was incubated at 200 rpm at 30° C. for 2 days. After this time 10 ml of the broth are added to 10 ml of fresh medium containing 200 µg/ml of daunorubicin and incubated as described above. The preceding step is repeated as necessary to obtain mutated bacteria. Those mutants were further isolated on the solid culture medium TA-1 (composition as follows).

| Solid culture medium TA-1 | |
|---|---|
| Ingredient | amount |
| glucose | 5 g |
| tryptone | 20 g |
| yeast extract | 5 g |
| NaCl | 0.5 g |
| agar | 15 g |
| $H_2O$ | 1 L |

Biotransformation of taxanes by mutated strains

The growth supporting nutrient medium S-7 is supplemented with 1% v/v on an aqueous extract of *Taxus canadensis*. This resulting supplemented medium is then inoculated with a thawed vial of a pure culture of one of our strain and incubated at 30° C. with constant shaking for a time sufficient to allow biotransformation of pro-taxanes.

The culture is then centrifuged and the remaining supernatant extracted with one volume of methylene chloride or ethyl acetate. After appropriate shaking, the organic fraction is evaporated to dryness under reduced pressure. The residue is then resolubilized in 50 ml of methylene chloride or ethyl acetate, and 50 ml of distilled water. After appropriate shaking, each fraction was collected and dried under reduced pressure. Each residues is dissolved in a measured minimal volume of HPLC grade methanol. All samples were kept frozen at −20° C. until analysis.

Samples were analyzed on HPLC using method no. 2. FIG. 13 shows HPLC chromatograms of *S. taxi, S. taxi* D200 and *S. taxi* D201 incubated the same time (48 hours) in the culture medium S-7 supplemented with 1% v/v of an aqueous extract of *Taxus canadensis*. All cultures had comparable cell density. This figure clearly illustrates the improved yields of biotransformation by the mutated strains *S. taxi* D200 and *S. taxi* D201. In FIGS. 14B and 14C the characteristic ultraviolet spectrum of the new pro-taxanes, produced by the mutated strains *S. taxi* D200 and *S. taxi* D201, are compared with the UV spectrum of two taxanes from *Taxus canadensis*.

The present invention will be more readily understood by referring to the following examples which are given to illustrate the invention rather to limit its scope.

EXAMPLE I

Mass Production of Paclitaxel using *Sphingomonas taxi*

A colony of a pure culture of *Sphingomonas taxi* is used to inoculate 5 ml of S-7 culture medium. The broth is incubated 2–3 days with constant shaking (90 rpm) at 22° C. This 5 ml is then transferred into 5 liters of the same culture medium. The resulting broth is incubated as described above in aerobic conditions.

After 4–5 days of incubation, or after the maximum cell density is reached, the cell pellet is separated by centrifugation. Hydrophobic compounds are then extracted from the supernatant by partition with one volume of dichloromethane. Each organic fraction is evaporated to dryness and, the residue is solubilized in a minimal amount of HPLC grade methanol, typically 500 µl to 1 ml.

Paclitaxel and taxanes are further purified by HPLC on a phenyl column using HPLC method no. 1. Typically, up to 400 11 of the methanolic solution are injected and fractions of 0.5 ml to 1 ml are collected. Fractions containing paclitaxel or taxanes are evaporated to dryness.

Using this method, from 200 ng to 1 µg of paclitaxel per liter of culture medium were purified.

EXAMPLE II

Mass Production of Taxanes and Paclitaxel using *Bacillus cereus* ssp. *taxi*

A thawed vial of a pure dense cell suspension of *Bacillus cereus* ssp. *taxi* is used to inoculate 500 ml of the defined medium for Bacillus. The broth is incubated 1 to 3 days with constant shaking (150 rpm) at 30° C. The cell pellet is then separated form the supernatant by centrifugation. Hydrophobic substances are extracted from the supernatant by an extraction with one volume of dichloromethane. The organic fraction is evaporated to dryness under reduced pressure, and residues resolubilized in a minimal amount of HPLC grade methanol.

Taxanes and paclitaxel are further purified on HPLC using method no. 2. Using this method, from 0.2 to 10 μg of paclitaxel can be produced, and from 0.2 to 15 μg of taxanes, including the specific bacterial taxane illustrated in FIG. 13B, can also be produced.

EXAMPLE III

Mass Production of Taxanes and Paclitaxel using *Bacillus megaterium* ssp. *taxi*

A thawed vial of a pure dense cell suspension of *Bacillus megaterium* ssp. *taxi* is used to inoculate 500 ml of the S-7 culture medium. The broth is incubated 1 to 3 days with constant shaking (150 rpm) at 30° C. The cell pellet is then separated form the supernatant by centrifugation. Hydrophobic substances are extracted from the supernatant by an extraction with one volume of dichloromethane. The organic fraction is evaporated to dryness under reduced pressure, and residues resolubilized in a minimal amount of HPLC grade methanol.

Taxanes and paclitaxel are further purified on HPLC using method no. 2. Using this method, from 1 to 12 μg of paclitaxel can be produced, and from 1 to 15 μg of taxanes, including the specific bacterial taxane illustrated in FIG. 13B, can also be produced.

EXAMPLE IV

Biotransformation of Pro-taxanes by *Sphingomonas taxi*

The growth supporting nutrient medium S-7 is supplemented with 1% v/v on an aqueous extract of *Taxus*

*canadensis*. This resulting supplemented medium is then inoculated with a thawed vial of a pure culture of one of *Sphingomonas taxi* and incubated at 30° C. with constant shaking for 24 to 96 hours. 1 The culture is then centrifuged and the remaining supernatant extracted with one volume of methylene chloride. After appropriate shaking, the organic fraction is evaporated to dryness under reduced pressure. The residue is then resolubilized in 50 ml of methylene chloride and 50 ml of distilled water. After appropriate shaking, the organic fraction is collected and dried under reduced pressure. The residue is dissolved in 500 µl of HPLC grade methanol and 100 µl of the methanolic solution are analyzed on HPLC using method no. 2 and compared to the resulting chromatogram of the organic extract of the growth-supporting nutrient medium supplemented with and aqueous extract of *Taxus canadensis* 1% v/v shaken the same time.

As illustrated in FIGS. 11, 12 and 14A, *Sphingomonas taxi* is able to biotransform taxanes into new pro-taxanes.

EXAMPLE V

Mutagenesis of *Sphingomonas taxi*

20 ml of the culture medium TA-1 with 200 µg/ml of daunorubicin (purchased from Rhône-Poulenc) were inoculated with 500 µl of an overnight culture of *Sphingomonas taxi*. The resulting broth was incubated at 200 rpm at 30° C. for 2 days. After this time 10 ml of the broth are added to 10 ml of fresh medium containing 200 µg/ml of daunorubicin and incubated as described above. The preceding step is repeated as necessary to obtain mutated bacteria. Those mutants were further isolated on the solid culture medium TA-1. Two new mutated strains were obtained named *Sphingomonas taxi* D200 and *Sphingomonas taxi* D201.

EXAMPLE VI

Biotransformation of taxanes by *Sphingomonas taxi* D200 and *Sphingomonas taxi* D201

The growth supporting nutrient medium S-7 is supplemented with 1% v/v on an aqueous extract of *Taxus canadensis*. This resulting supplemented medium is then inoculated with a thawed vial of a pure culture of one of our mutated strain and incubated at 30° C. at 150 rpm. Cultures were stopped after 24, 48 and 72 hours of incubation.

Cultures were then centrifuged and the remaining supernatants extracted with one volume of ethyl acetate. After appropriate shaking, the organic fractions were evaporated to dryness under reduced pressure. Residues were then resolubilized in 50 ml of ethyl acetate. After appropriate shaking, fractions were collected and dried under reduced pressure. Each residues were dissolved in a measured minimal volume of HPLC grade methanol. All samples were kept frozen at −20° C. until analysis.

Samples were analyzed on HPLC using method no. 2. FIG. 13 shows HPLC chromatograms of *S. taxi, S. taxi* D200 and *S. taxi* D201 incubated the same time (48 hours) in the culture medium S-7 supplemented with 1% v/v of an aqueous extract of *Taxus canadensis*. All cultures had comparable cell densities. This figure clearly illustrates the improved yields of biotransformation by the mutated strains *S. taxi* D200 and *S. taxi* D201. In FIG. 14B the characteristic ultraviolet spectrum of the new pro-taxanes produced by *S. taxi* D200 is compared with the UV spectrum of two taxanes from *Taxus canadensis*. FIG. 14C compares the UV spectrum of the new biotransformed taxane produce by *S. taxi* D201 with taxanes from the aqueous extract of *Taxus canadensis*.

While the invention has been described in connection with specific embodiments thereof, it will be understood that is capable of further modifications and this application is intended to cover any variations, uses, or adaptations of the invention following, in general, the principles of the invention and including such departures from the present disclosure as come within known or customary practice within the art to which the invention pertains and as many be applied to the essential features hereinbefore set forth, and as follows in the scope of the appended claims.

---

What is claimed is:

1. A process for producing a taxane, which comprises the steps of:
   a) culturing at least one bacterium isolated from plant species of Taxus in growth-supporting nutrient medium capable of promoting growth and reproduction of said bacteria, wherein said bacterium is selected from the group consisting of bacteria having all of the identifying characteristics of deposited strains ATCC deposit accession Nos. 202061, 202062, 202063, 202064, 202065, 202066, 202067, 202068. 202069, 202070, 202071, 202071, 202073 and mutants thereof having the taxane-producing characteristics of said deposited strains, and wherein said culturing is effected for a time sufficient to allow production of a taxane; and
   b) recovering a taxane from said bacteria or medium of step a).

2. The process of claim 1, wherein the plant species of Taxus is of the species selected from the group consisting of *Taxus canadensis, T. brevifolia, T. baccata, T. hunnewelliana* and *T. cuspidata*.

3. The process of claim 1, wherein said taxane produced is paclitaxel.

4. The process of claim 1, wherein said taxane is selected from the group consisting of paclitaxel, 10-deacetylcephalomannine, 7-epitaxol, 10-deacetyl-7-epitaxol, 7-epicephalomannine, baccatin III, 10-deacetylbaccatin III, cephalomannine, 7-epibaccatin III, 7-xylosyltaxol, 7-xylosyl-cephalomannine, taxagifine, 6-benzoyloxy taxagifine, 9-acetyloxy taxusin, 9-hydroxy taxusin, taxane Ia, taxane Ib, taxane Ic, taxane Id and any taxane corresponding to Formula I:

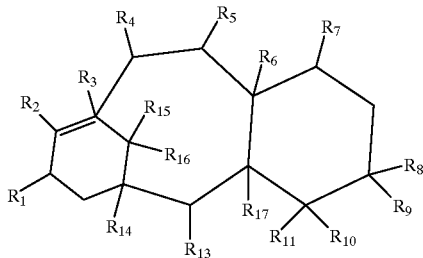

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ , $R_{15}$, $R_{16}$, $R_{17}$ are defined in Table 1.

5. The process of claim 1, wherein the taxane produced has the ultraviolet spectrum shown in FIG. 13, and the El spectrum shown in FIG. 14A.

6. The process of claim 1, wherein the bacterium has all of the identifying characteristics of deposited *Bacillus cereus* ssp. *taxi* strain ATCC deposit accession No. 202061.

7. The process of claim 1, wherein the bacterium has all of the identifying characteristics of deposited *Bacillus megaterium* ssp. *taxi* strain ATCC deposit accession No. 202062.

8. The process of claim 1, wherein bacterium has all of the identifying characteristics of deposited Pantoea sp. BCM 1 strain ATCC deposit accession No. 202071.

9. The process of claim 1, wherein the bacterium has all of the identifying characteristics of deposited Pantoea sp. BCM 2 strain ATCC deposit accession No. 202064.

10. The process of claim 1, wherein the bacterium has all of the identifying characteristics of deposited Pantoea sp. BCM 3 strain ATCC deposit accession No. 202070.

11. The process of claim 1, wherein the bacterium has all of the identifying characteristics of deposited *Bacillus cereus* ssp. BCM 4 strain ATCC deposit accession No. 202066.

12. The process of claim 1, wherein the bacterium has all of the identifying characteristics of deposited *Bacillus subtilis* ssp. *Taxi* strain ATCC deposit accession No. 20272.

13. The process of claim 1, wherein bacterium has all of the identifying characteristics of deposited *Bacillus megaterium* ssp. BCM 9 strain ATCC deposit accession No. 20265.

14. The process of claim 1, wherein the bacterium has all of the identifying characteristics of deposited Curtobacterium sp. BCM 5 strain ATCC deposit accession No. 20263.

15. The process of claim 1, wherein said growth-supporting nutrient medium include carbon sources, nitrogen sources, amino acids, vitamins and minerals.

* * * * *